US012042345B2

(12) United States Patent
Watson

(10) Patent No.: US 12,042,345 B2
(45) Date of Patent: Jul. 23, 2024

(54) DENTAL DEVICE COMPRISING SURGICAL TEMPLATE AND FALSE TEETH SET AND RELATED METHODS

(71) Applicants: Institut Straumann AG, Basel (CH); Jason Watson, La Cañada, CA (US)

(72) Inventor: Jason Watson, La Cañada, CA (US)

(73) Assignees: Institut Straumann AG, Basel (CH); Jason Watson, La Cañada, CA (US)

( * ) Notice: Subject to any disclaimer, the term of this patent is extended or adjusted under 35 U.S.C. 154(b) by 979 days.

(21) Appl. No.: 16/391,268

(22) Filed: Apr. 22, 2019

(65) Prior Publication Data

US 2019/0314114 A1 Oct. 17, 2019

Related U.S. Application Data

(63) Continuation of application No. 14/670,380, filed on Mar. 26, 2015, now abandoned.

(Continued)

(51) Int. Cl.

*A61C 1/08* (2006.01)
*A61B 6/03* (2006.01)
*A61B 6/51* (2024.01)
*A61C 8/00* (2006.01)

(Continued)

(52) U.S. Cl.

CPC .............. *A61C 1/084* (2013.01); *A61B 6/032* (2013.01); *A61B 6/51* (2024.01); *A61C 8/0009* (2013.01); *A61C 9/0046* (2013.01); *A61C 13/0004* (2013.01); *A61C 13/01* (2013.01); *A61C 13/08* (2013.01); *A61C 13/09* (2013.01); *A61C 8/0089* (2013.01); *A61C 2201/005* (2013.01)

(58) Field of Classification Search

CPC ......... A61C 1/084; A61C 1/085; A61C 1/082; A61C 1/00; A61C 1/009; A61C 1/0028; A61C 1/0048; A61C 1/005; A61C 1/0069; A61C 1/0075; A61C 8/0009; A61C 8/0046; A61C 8/00; A61C 13/0004; A61C 13/01; A61C 13/08; A61C 13/09

See application file for complete search history.

(56) References Cited

U.S. PATENT DOCUMENTS 5,098,296 A * 3/1992 Cullen ................ A61C 8/0048 433/173
5,503,557 A * 4/1996 Sillard ................ A61C 8/0048 433/172

(Continued)

FOREIGN PATENT DOCUMENTS

EP 2106768 7/2009

OTHER PUBLICATIONS

"Types of Implant Surgical Guides in Dentistry: A Review", by D'Souza, K.M., et al., J. Oral Implantol Oct. 2012; 38(5), pp. 643-652.

*Primary Examiner* — Yogesh P Patel
(74) *Attorney, Agent, or Firm* — Oliff PLC

(57) ABSTRACT

A dental device is described. The dental device includes a surgical template having one or more sites for drilling osteotomies in the maxillary or mandibular jaw and a false teeth set. The surgical template and false teeth set are configured to fit together to form a denture prosthesis that can be implanted in a patient. Also described are a method for creating a surgical dental template, a method for implanting a dental prosthesis, and a method for reducing jaw bone in a patient.

13 Claims, 47 Drawing Sheets

Related U.S. Application Data

(60) Provisional application No. 62/052,988, filed on Sep. 19, 2014, provisional application No. 61/971,804, filed on Mar. 28, 2014, provisional application No. 61/971,810, filed on Mar. 28, 2014.

(51) Int. Cl.

| | |
|---|---|
| ***A61C 9/00*** | (2006.01) |
| ***A61C 13/00*** | (2006.01) |
| ***A61C 13/01*** | (2006.01) |
| ***A61C 13/08*** | (2006.01) |
| ***A61C 13/09*** | (2006.01) |

(56) References Cited

U.S. PATENT DOCUMENTS

| | | | | |
|---|---|---|---|---|
| 5,556,278 | A | 9/1996 | Meitner | |
| 7,699,610 | B2 | 4/2010 | Childress | |
| 8,926,328 | B2 * | 1/2015 | Suttin | A61C 13/08 433/213 |
| 2003/0044749 | A1 | 3/2003 | Marotta | |
| 2006/0223029 | A1 * | 10/2006 | Berger | A61C 13/275 433/172 |
| 2009/0042167 | A1 | 2/2009 | Van Der Zel | |
| 2010/0183998 | A1 | 7/2010 | Poirier et al. | |
| 2010/0323325 | A1 * | 12/2010 | Berger | A61C 13/275 433/173 |
| 2012/0058449 | A1 * | 3/2012 | Sklarski | A61C 8/0048 700/98 |
| 2012/0214127 | A1 | 8/2012 | Drapeau et al. | |
| 2013/0130201 | A1 | 5/2013 | Smith et al. | |
| 2013/0203009 | A1 | 8/2013 | Mutsafi et al. | |
| 2014/0099600 | A1 | 4/2014 | Harrison | |
| 2014/0178839 | A1 * | 6/2014 | Berger | A61C 8/0048 433/173 |
| 2018/0000568 | A1 * | 1/2018 | Berger | A61C 13/275 |

* cited by examiner

STEP A

STEP B

STEP D

STEP F

STEP H

STEP G

V2R GUIDED SURGERY INFORMATION

| GENERAL PRACTITIONER INFORMATION | | | |
|---|---|---|---|
| FIRST NAME | ARTHUR | LAST NAME | DR. FORREST |
| EMAIL | ARTHUR@MSN.COM | | |

| CASE INFORMATION | | | | | | | | | | | | | | | | | |
|---|---|---|---|---|---|---|---|---|---|---|---|---|---|---|---|---|---|
| PATIENT'S NAME | DARIA MIX | 1 | 2 | 3 | 4 | 5 | 6 | 7 | 8 | 9 | 10 | 11 | 12 | 13 | 14 | 15 | 16 |
| PRESCRIPTIONS # | 1208222 | RIGHT | | | 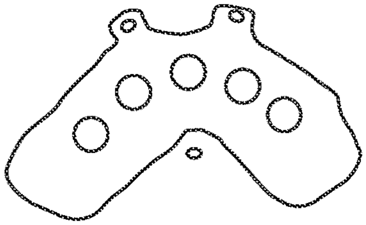 | | | | | | | | | | LEFT | | |
| ARCH | LOWER | | | | | | | | | | | | | | | | |
| TYPE | PARTIAL/FIXED | 32 | 31 | 30 | 29 | 28 | 27 | 26 | 25 | 24 | 23 | 22 | 21 | 20 | 19 | 18 | 17 |
| | | | | | | | | | | | | | | | | | |

| IMPLANT INFORMATION | | | | | | | | |
|---|---|---|---|---|---|---|---|---|
| | | | | | | | | |
| 5 TES | 29 | 28 | 27 | 22 | 21 | 20 | 19 | 18 |
| IMPLANT DIMENSIONS (mm) | 3.2 10 | 3.2 11 | 3.2 11 | 3.2 11 | 3.2 11 | 3.2 13 | 3.2 20 | 3.2 20 |
| SURGICAL KIT | 853710 | 853711 | 853712 | 853712 | 853715 | 853713 | 853710 | 853710 |
| DRILL WORKING LENGTH | 25 | 25 | 25 | 25 | 25 | 25 | 21 | 21 |
| SPECIAL NOTES | TEETHS 22, 25 SHOULD BE EXTRACTED PRIOR TO PLACING THE PIN GUIDE | | | | | | | |

GENERAL NOTES:
-GUIDES SHOULD BE FULLY SEATED
-ORDER TWO SETS OF TEMPORARY CYLINDERS IF YOU ARE GOING TO PICK UP THE RAPID APPLIANCE AT THE SURGICAL APPOINTMENT.
- WE RECOMMEND MUA COLLAR HEIGHTS BETWEEN 2mm - 3.5mm.

FIG. 24

V2R TREATMENT PLAN APPROVAL

| DOCTOR INFORMATION | | | |
|---|---|---|---|
| FIRST NAME: | | LAST NAME: | |
| PHONE NUMBER: | | EMAIL: | |
| CASE INFORMATION | | | |
| PATIENT'S FIRST NAME: | | PATIENT'S LAST NAME: | |
| PRESCRIPTION #: | | PATIENT'S DATE OF BIRTH: | |
| FULLY OR PARTIALLY: | | SINGLE OR DUAL PROTOCOL: | |

| APPROVAL METHOD | |
|---|---|
| **WHICH METHOD DID YOU USE TO VALIDATE THE TREATMENT PLAN?** | |
| ☐ | BLUE SKY PLAN IMPLANT PLANNING (FILE NAME:____________________) |
| ☐ | PDF PLANNING REPORT (FILE NAME: ____________________) |
| ☐ | ONLINE MEETING WITH V2R SPECIALIST (NAME OF THE SPECIALIST: __________) |

| APPROVAL | |
|---|---|
| ☐ | I CERTIFY THAT THE TREATMENT PLAN IS CORRECT. THIS FORM AUTHORIZES V2R TO PROCEED WITH THE V2R SURGICAL GUIDE CONCEPTION AND FABRICATION |
| ☐ | I WOULD LIKE V2R TO MODIFY THE IMPLANT PLANNING ACCORDING TO MY COMMENTS/REQUESTS<br>COMMENTS: |

SIGNATURE: ____________________ DATE: __________

FIG. 25

SCANNING INSTRUCTIONS

18.5 THE OCCLUSAL PLANE SHOULD BE PARALLEL TO THE PLANE OF IMAGE SLICE GENERATED, WITH NO TILT.

18.6 THE HEIGHT MUST BE SET IN ORDER TO CENTER THE OCCLUSAL PLANE IN THE FIELD OF VIEW (FOV).

18.7 IN CASE THAT BOTH ARCHES NEED TO BE TREATED, PLEASE PROVIDE A SEPERATE SCAN FOR EACH ARCH.

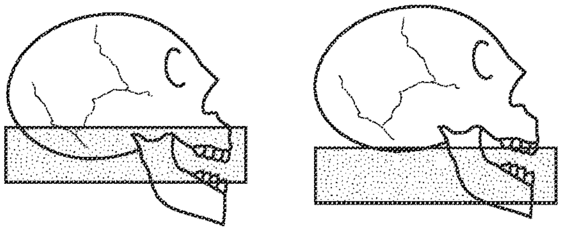

MAXILLA MANDIBLE

USE THE FOLLOWING SCANNING PARAMETERS TO PERFORM THE CT-SCAN:

| **PARAMETERS** | **VALUES** |
| --- | --- |
| GANTRY TILT | NONE (0°) |
| SLICE THICKNESS | MIN 0.2mm / MAX 0.4mm |
| RECONSTRUCTED SLICE INCREMENT | SAME AS SLICE THICKNESS |
| RECONSTRUCTION ALGORITHM | BONE |
| COMPRESSION | NONE |
| FORMAT | DICOM 3 |

FIG. 28C

REQUIREMENTS

- RENABUBG TEETH SHOULD BE CLEARLY VISIBLE [NO ARTIFACTS].
- UPPER AND LOWER TEETH SHOULD NOT TOUCH EACH OTHER.

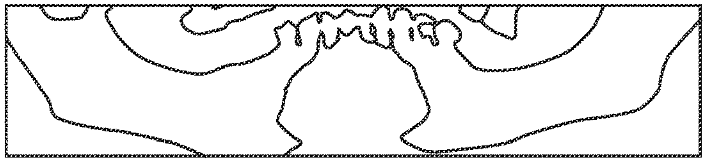

SENDING DATA TO V2R

THE FOLLOWING DATA MUST BE SENT TO V2R:

| **DATA** | **SHIPPING METHOD** |
| --- | --- |
| V2R PRESCRIPTION FORM | BY FAX (1.888.688.8421)<br>BY EMAIL (ORDER@V2RBIOMEDICAL.COM) |
| IMPRESSIONS + BITE REGISTRATION (1A) | MUST BE SENT **WITH A COPY OF THE PRESCRIPTION FORM** AT THE FOLLOWING ADDRESS:<br>V2R BIOMEDICAL<br>3012 IVAR AVENUE, ROSEMEAD, CA 91770 |
| DICOM FILES<br>• SCAN OF THE PATIENT (1B) | BY FOLLOWING THE V2R FILE TRANSFER INSTRUCTIONS (AT THE END OF THE DOCUMENT) |

IF YOU WOULD LIKE V2R TO BE IN CHARGE OF THE RESTORATION, PLEASE CONTACT OUR SALES DEPARTMENT (1.800.369.5485)

FIG. 28D

SCANNING INSTRUCTIONS

28.6 THE OCCLUSAL PLANE SHALL BE PARALLEL TO THE PLANE OF IMAGE SLICE GENERATED, WITH NO TILT.

28.7 THE HEIGHT MUST BE SET IN ORDER TO CENTER THE OCCLUSAL PLANE IN THE FIELD OF VIEW (FOV).

28.8 IN CASE THAT BOTH ARCHES NEED TO BE TREATED, PLEASE PROVIDE A SEPARATED SCAN FOR EACH ARCH.

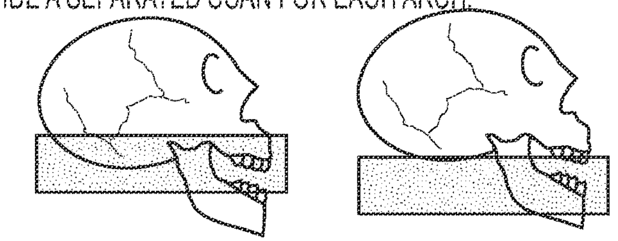

USE THE FOLLOWING SCANNING PARAMETERS TO PERFORM THE CT-SCAN:

| PARAMETERS | VALUES |
|---|---|
| GANTRY TILT | NONE (0°) |
| SLICE THICKNESS | 0.4mm (MAXIMUM) |
| RECONSTRUCTED SLICE INCREMENT | SAME AS SLICE THICKNESS |
| RECONSTRUCTION ALGORITHM | BONE |
| COMPRESSION | NONE |
| FORMAT | DICOM 3 |

REQUIREMENTS

- AT LEAST XXX XXXXXXXXXXXXXXXXXXXXXXXXXXXXXXXX THE CT-SCAN IMAGES. PLEASE XXXX XXXX XXXX "LOST" IN POSSIBLE ARTIFACTS CREATED BY EXISTING XXXX

FIG. 29C

2C. CT-SCAN OF THE RADIOGRAPHIC GUIDE WITH THE MASTER MODEL

SCANNING INSTRUCTIONS

2C.1 THE RADIOGRAPHIC GUIDE MUST BE INSTALLED PRECISELY ONTO THE MASTER MODEL.

2C.2 THE RESULTING ASSEMBLY MUST BE PLACED IN THE SCANNER IN A POSITION SIMILAR TO ITS POSITION DURING THE PATIENT SCAN.

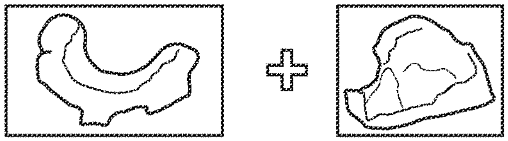

2C.3 THE RESULTING ASSEMBLY MUST BE SUPPORTED BY A HIGHLY TRANSLUCENT MATERIAL (SUCH AS POLYETHYIENE OR POLYURETHANE FOAMS).

USE THE FOLLOWING SCANNING PARAMETERS TO PERFORM THE CT-SCAN:

| PARAMETERS | VALUES |
|---|---|
| GANTRY TILT | NONE (0°) |
| SLICE THICKNESS | MIN 0.2mm / MAX 0.4mm |
| RECONSTRUCTED SLICE INCREMENT | SAME AS SLICE THICKNESS |
| RECONSTRUCTION ALGORITHM | BONE |
| COMPRESSION | NONE |
| FORMAT | DICOM 3 |

NOTE:

IF BOTH ARCHES ARE TO BE TREATED, PLEASE PROCEED TO SCAN ONE ASSEMBLY AT A TIME.

FIG. 29D

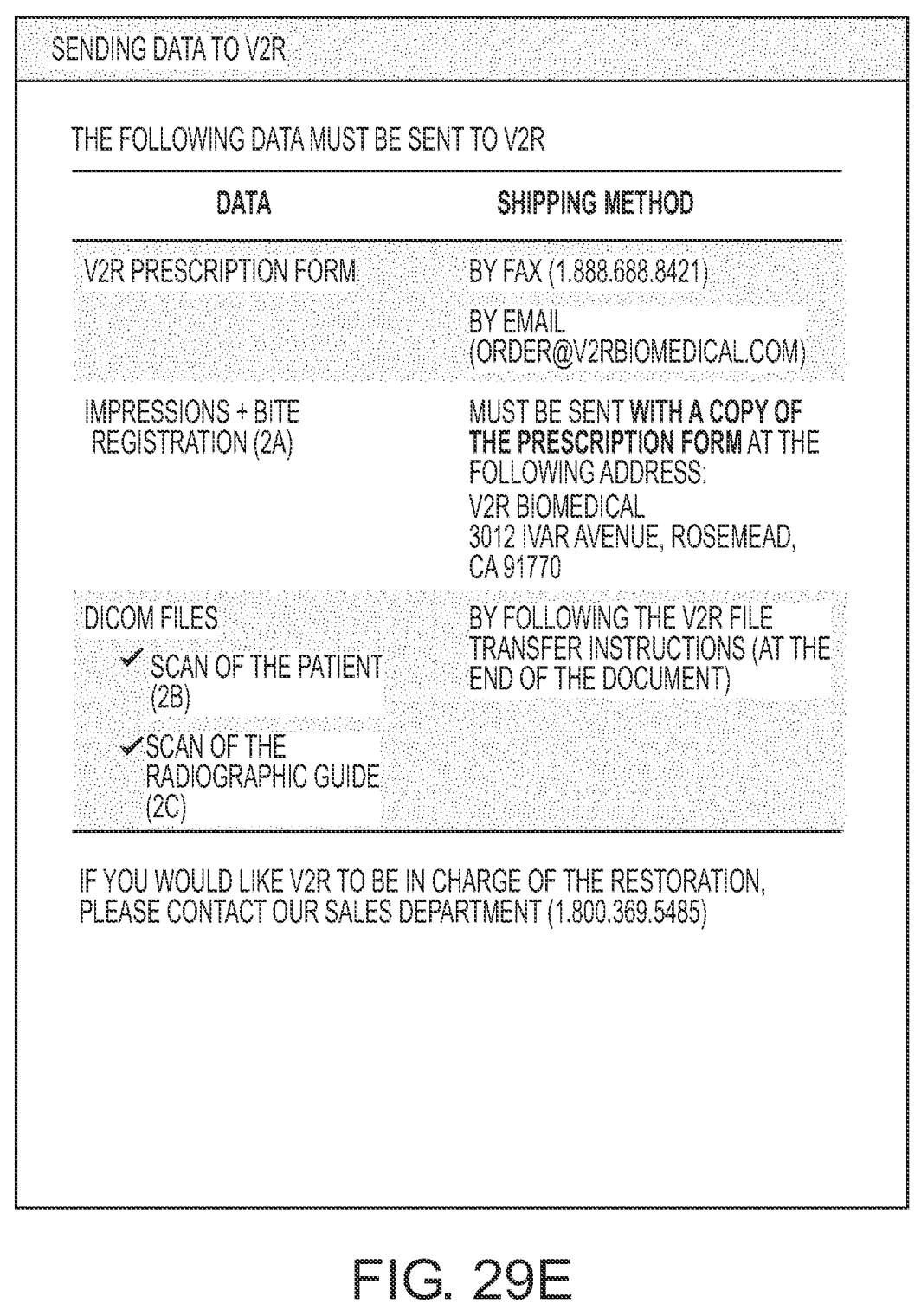

SENDING DATA TO V2R

THE FOLLOWING DATA MUST BE SENT TO V2R

| DATA | SHIPPING METHOD |
|---|---|
| V2R PRESCRIPTION FORM | BY FAX (1.888.688.8421)<br>BY EMAIL (ORDER@V2RBIOMEDICAL.COM) |
| IMPRESSIONS + BITE REGISTRATION (2A) | MUST BE SENT **WITH A COPY OF THE PRESCRIPTION FORM** AT THE FOLLOWING ADDRESS:<br>V2R BIOMEDICAL<br>3012 IVAR AVENUE, ROSEMEAD, CA 91770 |
| DICOM FILES<br>✓ SCAN OF THE PATIENT (2B)<br>✓ SCAN OF THE RADIOGRAPHIC GUIDE (2C) | BY FOLLOWING THE V2R FILE TRANSFER INSTRUCTIONS (AT THE END OF THE DOCUMENT) |

IF YOU WOULD LIKE V2R TO BE IN CHARGE OF THE RESTORATION, PLEASE CONTACT OUR SALES DEPARTMENT (1.800.369.5485)

FIG. 29E

3A. FULL ARCH IMPRESSION

3A.1 MAKE AN ACCURATE IMPRESSION OF THE ARCH TO BE TREATED.

NOTE:

THIS IMPRESSION WILL LATER BE USED TO POUR A MASTER MODEL IN ORDER TO VALIDATE THE FIT OF THE SURGICAL GUIDE. IT IS THEREFORE IMPORTANT TO PROVIDE ACCURATE IMPRESSIONS.

3B. DENTURE WITH MARKERS

3B.1 EXAMINE THE DENTURE OF YOUR PATIENT TO DECIDE IF YOU CAN USE IT TO PERFORM THE DUAL SCAN PROTOCOL.

THE IDEAL DENTURE SHOULD HAVE:

- TEETH OF PROPER SIZE, SHAPE AND LENGTH
- WELL ESTABLISHED OCCLUSION
- BUCCAL FLANGES WIDE ENOUGH FOR GUTTA-PERCHA MARKERS AND RETENTIVE PINS POSITIONING
- HARD REFINE ONLY
- SECURE AND CLOSE FIT TO SOFT TISSUE AND PATIENT CAST
- NO RADIO-OPAQUE (LIKE TRIAD FROM DENTSPLY) OR METAL MATERIALS

FIG. 30A

⚠ WARNING:

IF THE ACTUAL DENTURE DOES NOT MEET THE IDEAL DENTURE CRITERIA THAT ARE MENTIONED ABOVE, PLEASE MAKE A NEW ONE BEFORE DOING THE SCAN ACQUISTION.

THE V2R GUM-SUPPORTED SURGICAL GUIDE IS DESIGNED FROM THE SHAPE OF THE DENTURE. IT IS THEREFORE ESSENTIAL TO WORK FROM A DENTURE OF GOOD QUALITY IN ORDER TO GET A SAFE AND ACCURATE SURGICAL GUIDE IN RETURN.

38.2 INSERT 6 OR MORE RADIO-OPAQUE MARKERS ON THE OUTER SURFACE OF THE DENTURE:

- USE THE #3 ROUND BUR TO CREATE AT LEAST 6 SMALL HOLES ON THE FLANGES OF THE OUTER SURFACE OF THE DENTURE - SOME CLOSE TO THE TOOTH-GINGIVA BORDER, OTHERS CLOSE TO THE OUTER BORDER.

- DRILL SPHERICAL HOLES OF 1mm DEEP AND 1-1.5mm DIAMTER. AVOID MAKING THE HOLES LARGER THAN INDICATED (LARGER VOLUME OF RADIO-OPAQUE MATERIAL MIGHT CAUSE ARTIFACTS).

- FILL HOLES WITH A RADIO-OPAQUE MATERIAL (PREFFERED MATERIAL IS GUTTA-PERCHA).

- PLAN MARKER POSITIONS EVENLY ON LINGUAL/PALATAL AND BUCCAL/LABIAL REGIONS. PREFERRED POSITIONS OF THE MARKERS ON THE DENTURE (CASE OF SIX MARKERS):

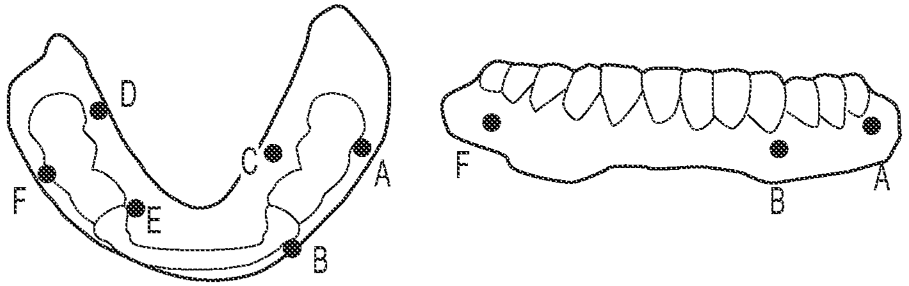

- ENSURE MARKERS ARE RANDOMLY DISTRIBUTED IN SEVERAL PLANES.

AVOID PLACING MARKERS ON THE INNER SURFACE OF THE DENTURE.

FIG. 30B

NOTE:

RADIO-OPAQUE MARKERS ARE USED TO FACILITATE THE MERGE OF THE SCANNED DENTURE TO THE CT-SCAN OF THE PATIENT WEARING THE DENTURE.

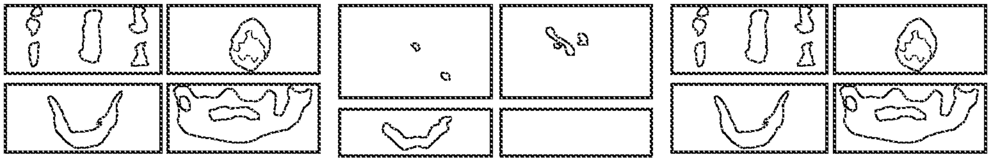

3C. CT-SCAN OF THE PATIENT WEARING THE DENTURE

PREPARATION OF THE PATIENT

3C.1 PATIENT MUST REMOVE ALL METAL PROTHESIS, AS WELL AS METAL JEWELLERY THAT MIGHT INTERFERE WITH THE REGION TO BE SCANNED.

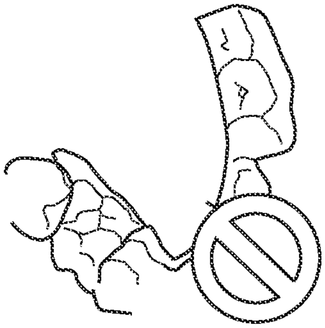

3C.2 PATIENT SHOULD BE IN A STATIC POSITION, WITH THE HEAD UPRIGHT.

3C.3 PATIENT MUST WEAR THE GUTTA-PERCHA FILLED DENTURE.

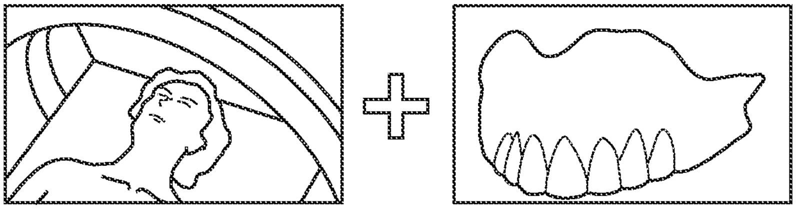

3C.4 PATIENT SHOULD BITE FIRMLY IN CENTRIC OCCLUSION.

3C.5 PATIENT MUST NOT MOVE OR SWALLOW DURING THE SCAN ACQUISITION.

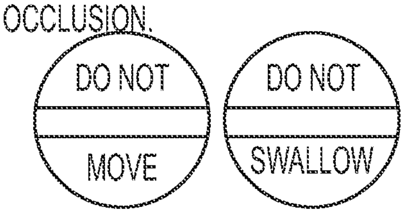

FIG. 30C

⚠ WARNING:

IF THE PATIENT IS SCANNED WITHOUT YOUR PRESENCE, PRACTICE THE CORRECT SEATED POSITION OF THE DENTURE WITH THE PATIENT.

SCANNING INSTRUCTIONS

3C.6 THE OCCLUSAL PLANE SHOULD BE PARALLEL TO THE PLANE OF IMAGE SLICE GENERATED, WITH NO TILT.

3C.7 THE HEIGHT MUST BE SET IN ORDER TO CENTER THE OCCLUSAL PLANE IN THE FIELD OF VIEW (FOV).

3C.8 IN CASE THAT BOTH ARCHES NEED TO BE TREATED, PLEASE PROVIDE A SEPARATE SCAN FOR EACH ARCH.

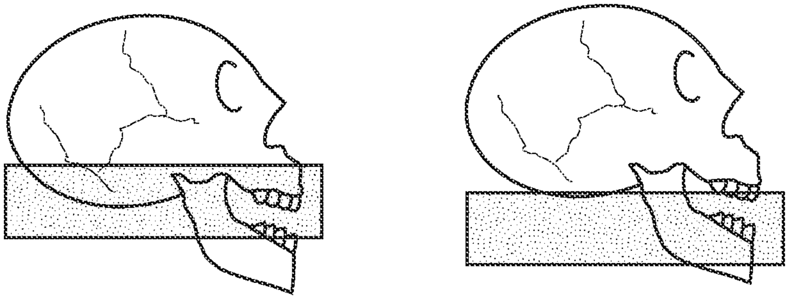

MAXILLA MANDIBLE

USE THE FOLLOWING SCANNING PARAMETER TO PERFORM THE CT-SCAN:

| PARAMETERS | VALUES |
|---|---|
| GANTRY TILT | NONE (0°) |
| SLICE THICKNESS | MIN 0.2mm / MAX 0.4mm |
| RECONSTRUCTED SLICE INCREMENT | SAME AS SLICE THICKNESS |
| RECONSTRUCTION ALGORITHM | BONE |
| COMPRESSION | NONE |
| FORMAT | DICOM 3 |

FIG. 30D

REQUIREMENTS

- RADIO-OPPAQUE MARKERS MUST BE DISTINGUISHABLE ON THE CT-SCAN IMAGES.

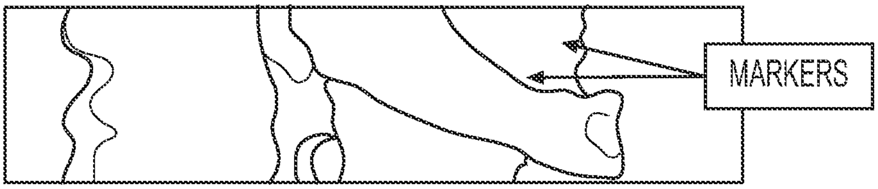

3D. CT-SCAN OF THE DENTURE ALONE

SCANNING INSTRUCTIONS

3D.1 THE DENTURE SHOULD BE SCANNED IN A POSITION SIMILAR TO ITS POSITION DURING THE PATIENT SCAN.

3D.2 THE DENTURE MUST BE SUPPORTED BY A HIGHLY TRANSLUCENT MATERIAL (SUCH AS POLYETHYLENE OR POLYURETHANE FOAMS).

USE THE FOLLOWING SCANNING PARAMETERS TO PERFORM THE CT-SCAN:

| PARAMETERS | VALUES |
|---|---|
| GANTRY TILT | NONE (0°) |
| SLICE THICKNESS | 0.3 mm PREFERABLY |
| | MIN 0.2mm / MAX 0.4mm |
| RECONSTRUCTED SLICE INCREMENT | SAME AS SLICE THICKNESS |
| RECONSTRUCTION ALGORITHM | BONE |
| COMPRESSION | NONE |
| FORMAT | DICOM 3 |

NOTE:

IF BOTH ARCHES ARE TO BE TREATED, PLEASE PROCEED TO SCAN ONE DENTURE AT A TIME.

FIG. 30E

SENDING DATA TO V2R

THE FOLLOWING DATA MUST BE SENT TO V2R

| DATA | SHIPPING METHOD |
|---|---|
| V2R PRESCRIPTION FORM | BY FAX (1.888.688.8421)<br>BY EMAIL (ORDER@V2RBIOMEDICAL.COM) |
| IMPRESSIONS (3A) | MUST BE SENT **WITH A COPY OF THE PRESCRIPTION FORM** AT THE FOLLOWING ADDRESS:<br>V2R BIOMEDICAL<br>3012 IVAR AVENUE, ROSEMEAD, CA 91770 |
| DICOM FILES<br>• SCAN OF THE PATIENT (3C)<br>• SCAN OF THE DENTURE ALONE (3D) | BY FOLLOWING THE V2R FILE TRANSFER INSTRUCTIONS (AT THE END OF THE DOCUMENT) |

IF YOU WOULD LIKE V2R TO BE IN CHARGE OF THE RESTORATION, PLEASE CONTACT OUR SALES DEPARTMENT (1.800.369.5485)

FIG. 30F

1. BEFORE SENDING ANY SCAN DATA, PLEASE MAKE SURE THAT THE CASE PRESCRIPTION WAS PREVIOUSLY SENT TO V2R BIOMEDICAL (BY FAX: 855.432.2850 OR EMAIL: ORDER@V2RBIOMEDICAL.COM).

2. CREATE A .ZIP ARCHIVE WITH EACH MAIN FOLDER CONTAINING THE DICOM FILE SERIES, FOR A DOUBLE SCAN, THERE SHOULD BE 2 SEPARATE MAIN FOLDERS, SO YOU SHOULD CREATE A .ZIP ARCHIVE FOR EACH.

HOW TO COMPRESS AND UNCOMPRESS FILES (ZIP FILES) ON WINDOWS

A. LOCATE THE FILE OR FOLDER THAT YOU WANT TO COMPRESS.

B. RIGHT-CLICK THE FILE OR FOLDER, POINT TO SEND TO, AND THEN CLICK COMPRESSED (ZIPPED) FOLDER.

A NEW COMPRESSED FOLDER IS CREATED. TO RENAME IT, RIGHT-CLICK FOLDER, CLICK RENAME, AND THEN TYPE THE NEW NAME.

3. IDENTIFY THE .ZIP FILES BY RENAMING THEM: "LAST_FIRST_PATIENT.ZIP" FOR THE PATIENT SCAN AND "LAST_FIRST_PROSTHESIS.ZIP" FOR THE PROSTHESIS ONLY SCAN (IF APPLICABLE).

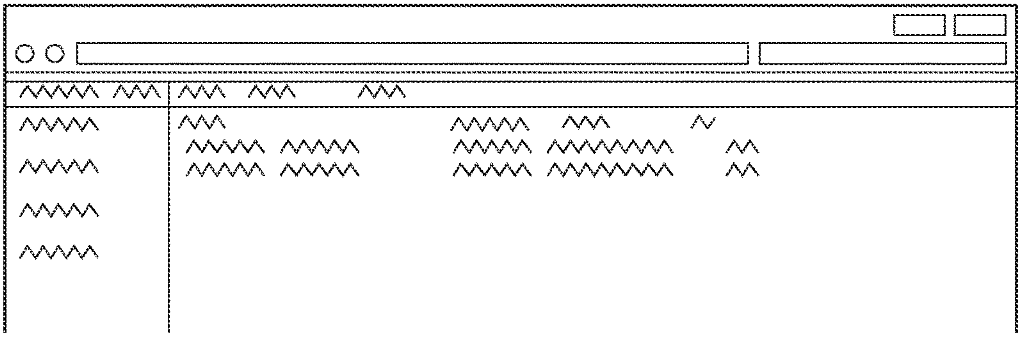

FIG. 31A

6. ADD THE SECOND .ZIP ARCHIVE (IF FOR A DOUBLE SCAN)
7. ADD "ORDER@V2RBIOMEDICAL.COM" EMAIL ADDRESS IN THE SECOND BOX
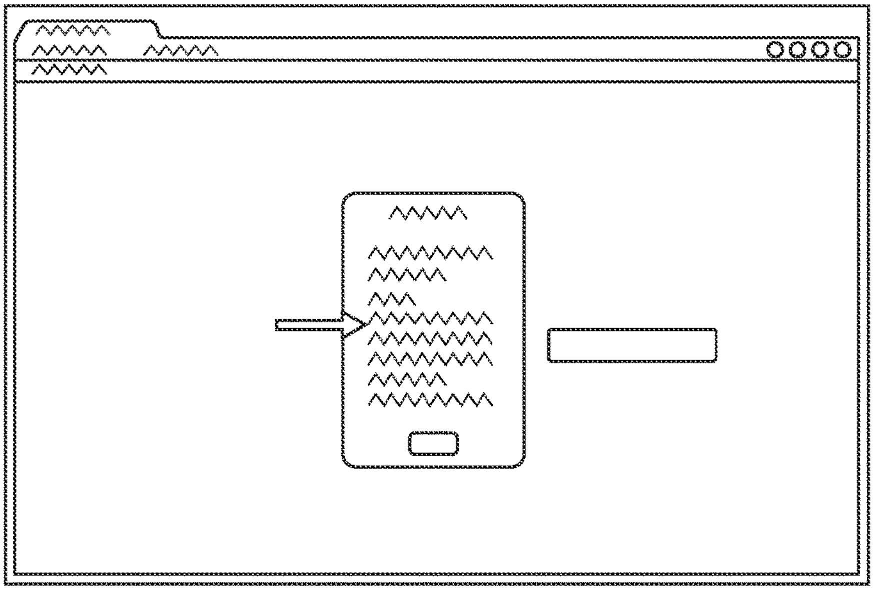
8. ADD YOUR EMAIL IN THE THIRD BOX.
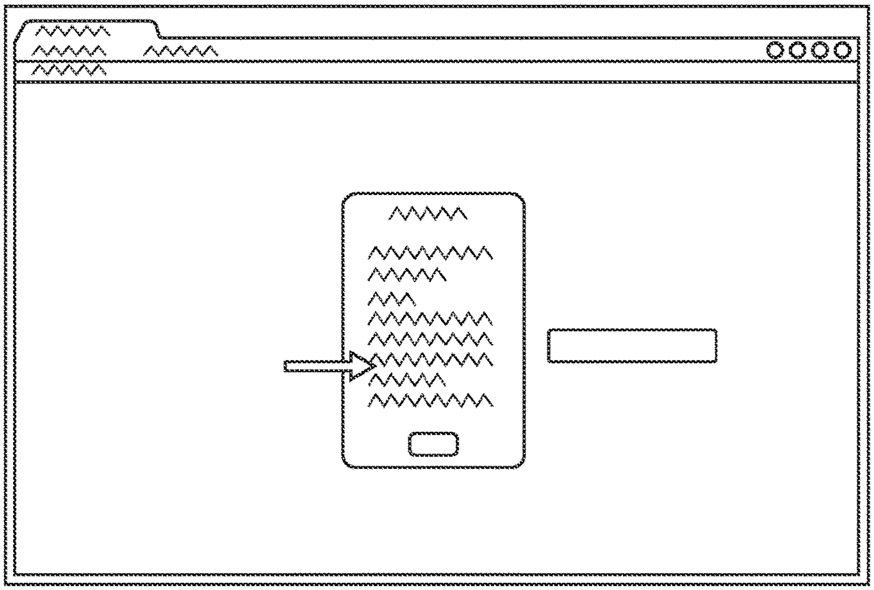
FIG. 31C 9. CLICK TRANSFER AND WAIT FOR THE TRANSFER CONFIRMATION BEFORE CLOSING THE WINDOW.
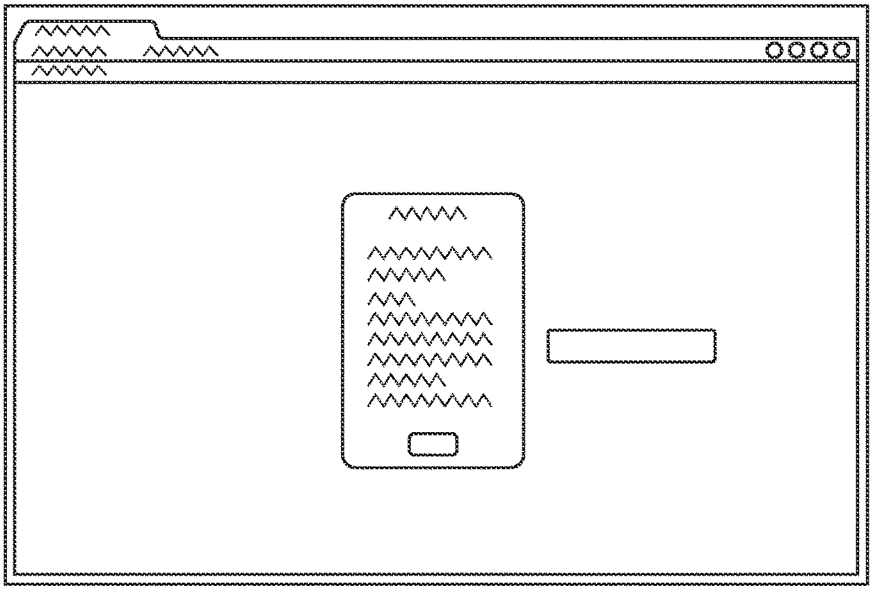
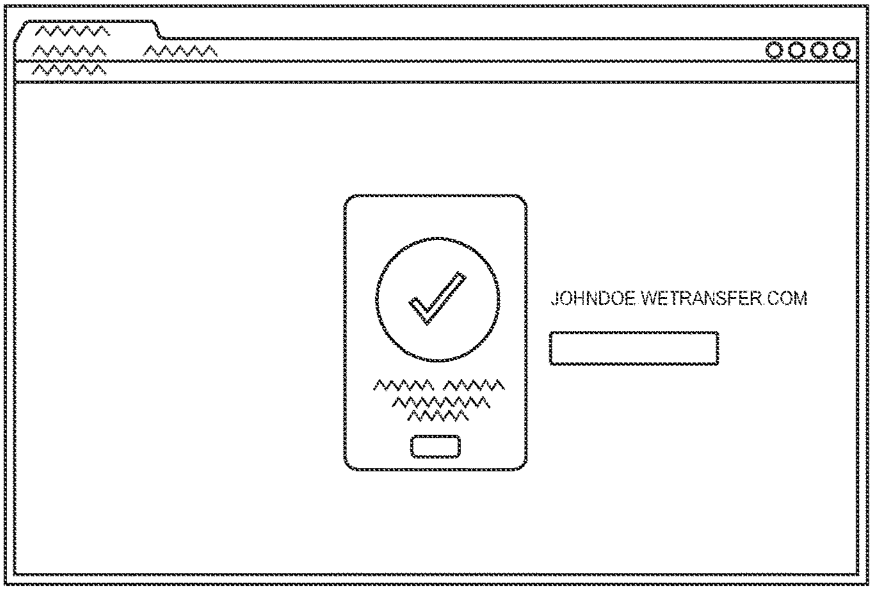
FIG. 31D

DENTAL DEVICE COMPRISING SURGICAL TEMPLATE AND FALSE TEETH SET AND RELATED METHODS

CROSS-REFERENCE TO RELATED APPLICATIONS

This Continuation application relies on the disclosure of and claims priority to and the benefit of the filing date of U.S. patent application Ser. No. 14/670,380 filed on Mar. 26, 2015, which claims priority to and the benefit of the filing dates and Provisional Application No. 61/971,804 and U.S. Provisional Application No. 61/971,810, both filed on Mar. 28, 2014, and U.S. Provisional Application No. 62/052,988, filed Sep. 19, 2014, the disclosures of which are hereby incorporated by reference herein in their entireties.

BACKGROUND OF THE INVENTION

Field of the Invention

The present invention relates to the field of dental surgery. More particularly, the present invention relates to a combination surgical template and false teeth set that fit together to form an implantable denture. The present invention also relates to methods for manufacturing a surgical dental template, methods for installing a denture prosthesis in a partially edentulous patient, and method for reducing jaw bone in a patient.

Description of Related Art

The use of dental prostheses with dental implants secured in the upper or lower jawbone is well known in the art. Accurate placement of the implants within the jawbone is a difficult task. The dental surgeon typically has difficulty deciding on a drilling axis for the implants since the ideal position for the implants should be decided with knowledge of the jawbone structure into which the implant is to be inserted, and with knowledge of the position within the jawbone structure of the nerve tissue, the gum surface and the required position and dimensions of the false teeth or dentures to be supported by the dental implant.

The conventional surgical procedure for installing one, implant-supported, prosthetic tooth includes drilling a properly positioned hole in the jawbone of the patient, inserting the implant in the hole, and attaching the prosthetic tooth to the implant. Proper implant positioning is also extremely important to ensure that the implant is anchored within sufficient bone structure in the patient's jawbone.

The most common method for locating a dental implant hole is to visually survey the area and drill the hole in a freehand manner. However, this method can readily result in imperfect bores due to space limitations associated with working inside a patient's mouth. If the drilling axis is not properly chosen, the installed implants might cause damage to the tissues and muscle surrounding the area of implantation and subsequently cause temporary or permanent paresthesia. Furthermore, other problems can result from flawed or imperfect implant holes, such as uneven force distribution, insufficient bone growth around the implant, secondary infections, and ultimately, implant failure.

During a one-stage surgical procedure, a healing abutment assists in the healing, formation, and maintenance of the soft tissue over the implant while bone integration occurs. The healing abutment is immediately placed into the implant well to ensure that the gum line will heal properly and look natural once the final abutment is tapped into the implant.

During a two-stage surgical procedure, a cover screw is initially screwed into the implant well. The tissue surrounding the cover screw is then sutured to protect the implant site while bone integration occurs. Once the bone has integrated, an incision is made in the tissue above the site, at which time integration is checked. Once the bone has healed properly, the cover screw is then removed, and a healing abutment is screwed into the implant well. With the healing abutment securely in place the tissue surrounding the area is sutured. Approximately 4-6 weeks later, the healing abutment can be removed and a final abutment is then placed into the implant. In some surgical cases, a final abutment is immediately placed into the implant well rather than the healing abutment and sutures are not required. In both the one-stage and two-stage surgical procedure, the final abutment supports the final crown or denture.

Many types of surgical guides are on the market today. They can be tooth supported, gum supported, or bone supported. The simplest guides are done in the laboratory. They consist of acrylic templates (or stents), or teeth, both filled with radiopaque markers that provide the position of the teeth in relation to the bone on 2D radiographs. Holes are drilled through these surgical guides at the selected implant sites and the surgeon uses them to make bone perforations. Afterwards, the surgeon needs to raise a flap in order to make the osteotomies. Examples of such guides are shown in FIG. 1 and FIGS. 2A-2B. More sophisticated guides use computer tomography (CT)-scan data and special software in order to place the implants according to three-dimensional (3D) data. The guide is then fabricated using stereolithographic machines or milling machines.

Each surgical stent commonly used is custom-built and these devices are only useful for a single patient, are costly to fabricate, and they require a number of intermediary office and laboratory steps to take an impression of the patient's arch and create a cast model from which the surgical stent is formed.

Superstructures are used as load-bearing elements that interface prosthesis to implants. In the conventional method for the construction of superstructures, a physical model of the patient's gums and dental implant heads is prepared on which the superstructure is built manually using molding and other techniques known in the art. The craftsman or technician skilled at manufacturing such dental superstructures takes into consideration the size and shape of the desired dentures to be placed over the superstructure when crafting the same. The procedure for manufacturing dental implant superstructures as is conventionally known in the art is time-consuming and sometimes results in imperfect structures or defects in the visual appearance of the dentures to be placed over the superstructure.

Therefore, in an effort to reduce costs and the number of steps associated with fabricating a traditional surgical stent, various forms of prefabricated surgical stents and positioning guide systems have been developed to aid the dental surgeon. In International patent application publication no. WO 94/26200, there is described an adjustable guiding device for positioning dental implants in which it is possible for the dental surgeon to adjust a drilling axis for each implant before proceeding to use the guiding device or drill template to guide the surgeon's drill for the purposes of preparing the drill hole for the implant.

In U.S. Pat. No. 5,401,170, there is disclosed a method and apparatus for measuring by camera image the implant heads of the implants in the patient's mouth for the purposes of cutting a frame on which the prosthetic teeth will be arranged and baked. In the method disclosed, the construction of the frame or superstructure is carried out in the absence of a reference to the shape and position of the patient's ideal tooth position.

Thus, as the dentures or artificial teeth are crafted on the frame or superstructure, care would be required during the manual process to ensure that the position of the teeth on the frame will match the opposed set of teeth in the patient's mouth.

It would thus be desirable to provide a drill guide system comprising components fabricated prior to the actual surgery that may be used more than once for the same patient, for any restoration configuration, and that enables precise implant spacing, and also ensures that the implant holes are drilled at the proper angle and orientation.

SUMMARY OF THE INVENTION

One embodiment of the invention comprises a dental device comprising a surgical template having one or more sites for drilling osteotomies in the maxillary or mandibular jaw and a false teeth set. For such dental device, the surgical template and false teeth set may be configured to fit together to form a denture prosthesis that may be implanted in a patient to provide for the appearance of natural teeth.

In embodiments, the surgical template may be configured to fit over an edentulous patient's maxillary or mandibular gum tissue, and a portion of the surgical template may have the appearance of gum tissue.

In embodiments, the one or more sites may be openings each providing a channel for drilling an osteotomy into the maxillary or mandibular jaw. Further, each opening may comprise a cylindrical wall having a height which is capable of limiting the drilling depth of the osteotomy. In additional embodiments, the false teeth set comprises one or more openings configured to overlap the one or more openings of the surgical template when the template and false teeth set are fit together.

In embodiments, the surgical template and false teeth set may have male and female portions capable of interlocking. In one embodiment, the surgical template comprises a male portion configured to interlock with a female portion on one of the teeth of the false teeth set. In another embodiment, the surgical template comprises a ledge configured to fit the false teeth set.

In additional embodiments, the surgical template comprises one or more sets of drill holes configured to provide a guide for reducing jaw bone when the surgical template is positioned on the maxillary or mandibular jaw during use.

In additional embodiments, a wall of the surgical template is configured to form one or more pin holes. The one or more pin holes may be configured as projections extending outward from a wall of the surgical template. The device may further comprise pins passing though each of the pin holes. Each pin may have a handle portion extending outward from each projection and a tapered portion extending inward through each projection. In additional embodiments, the surgical template may comprise one or more flanges extending outward from the template.

Another embodiment of the invention comprises a dental device comprising a surgical template configured to fit the interior of a maxillary or mandibular jaw over an edentulous patient's maxillary or mandibular gum tissue and a false teeth set. In embodiments the surgical template and false teeth set may be configured to fit together. The surgical template may comprise one or more openings each providing a channel for drilling an osteotomy into the maxillary or mandibular jaw. Further, the false teeth set may comprise one or more openings configured to overlap the one or more openings of the surgical template when the template and false teeth set are fit together. Further, a wall of the surgical template may be configured to form one or more pin holes and the device may further comprise pins passing though each of the pin holes.

Another embodiment of the invention comprises a dental device comprising a surgical template configured to fit over the gum tissue of a partially edentulous jaw missing one or more incisors, the surgical template having one or more openings each providing a channel for drilling an osteotomy into the maxillary or mandibular jaw at the site of the missing incisors and one or more removable false teeth configured to fit the surgical template at each opening. In embodiments, the surgical template and one or more removable false teeth provide a partial or complete bridge between the left and right cuspids when implanted into a patient's jaw. In embodiments, the surgical template may be configured to partially wrap around the left and right cuspids.

Another embodiment of the invention comprises a method for creating a surgical dental template, comprising performing a CT scan on a patient, transferring one or more CT scan images into treatment planning software, virtually placing implants in one or more positions on the CT scan using the treatment planning software, and creating a surgical template based on the positions on the CT scan that provide one or more sites for drilling osteotomies in the maxillary or mandibular jaw for installing the implants. In embodiments, the CT scan slices implant or anchor sites by size and diameter per zone into the jaw bone.

Another embodiment of the invention comprises a method for implanting a denture prosthesis in a patient, comprising creating a treatment planning protocol according to the treatment planning software and implanting the surgical template in the patient according to the treatment planning protocol.

In embodiments, the surgical template is configured to fit over an edentulous patient's maxillary or mandibular gum tissue. In embodiments, a portion of the surgical template has the appearance of gum tissue.

In embodiments, the one or more sites are openings each providing a channel for drilling an osteotomy into the maxillary or mandibular jaw. Each opening may comprise a cylindrical wall having a height which is capable of limiting the drilling depth of the osteotomy.

In embodiments, the one or more CT scan images are in the form of DICOM files.

In embodiments, the surgical template may be manufactured from a nanoceramic composite.

In embodiments, the surgical template is manufactured through CNC milling.

In embodiments the patient is fully edentulous, and the CT scan is performed with the patient wearing a denture with radio-opaque markers. In other embodiments, the patient is partially edentulous, and the CT scan is performed with the patient wearing a radiographic guide. In other embodiments, the patient is partially edentulous, and the CT scan is performed with the patient not wearing a radiographic guide.

In embodiments, the method further comprises making a set of full arch impressions from the patient's jaw; performing a CT scan on the arch impressions; and creating a surgical template based on the CT scan of the arch impressions.

In embodiments, the surgical template is configured to fit with a false teeth set to form a denture prosthesis.

In embodiments, the false teeth set comprises one or more openings configured to overlap the one or more openings of the surgical template when the template and false teeth set are fit together.

Another embodiment of the invention comprises a method for implanting or installing a denture prosthesis in a partially edentulous patient. The method may first comprise providing a surgical template and a false teeth set. The surgical template is configured to fit over the gum tissue of an edentulous jaw of a patient and has one or more sites for drilling osteotomies, and the surgical template and false teeth set are configured to fit together to form a denture prosthesis. The surgical template is then positioned over the gum tissue of an edentulous jaw of a patient at a first position and the false teeth may be inserted and set into the surgical template. The false teeth set may be fixed into the surgical template with a composite. The patient is then instructed to bite down on the false teeth set with natural teeth of the jaw opposite the edentulous jaw. The surgical template is repositioned, and the steps are repeated until the patient confirms occlusion between the natural teeth and false teeth set. The surgical template is finally fixed over the gum tissue of the patient's edentulous jaw at a second position.

In embodiments, a wall of the surgical template is configured to form one or more pin holes, the surgical template comprising pins passing though each of the pin holes, and the pins are used to fix the surgical template over the gum tissue of the patient's edentulous jaw.

In embodiments, the method further comprises drilling osteotomies into the edentulous jaw based on the drilling sites and installing implants at the osteotomies and securing the surgical template through the implants. The implants can be secured with a fastener.

In embodiments, the surgical template and false teeth can be finished or converted to provide the appearance of a dental prosthesis by removing one or more of a boundary line between the surgical template and false teeth set, one or more pin holes in the surgical template, and one or more flanges in the surgical template. The boundary line and one or more pin holes can be removed by filling with composite.

Another embodiment of the invention comprises a method for reducing jaw bone. A surgical template configured to fit the interior of a maxillary or mandibular jaw over an edentulous patient's gum tissue is installed in a patient. The surgical template has one or more sets of drill holes. Next, osteotomies may be perforated through the drill holes in the surgical template to define markings in the jaw bone forming a boundary for reducing bone. The surgical template is removed and the jaw bone is exposed though an incision to reveal the osteotomies. Finally, a surgical instrument is used to remove jaw bone based on the boundary formed by the markings.

The device of the invention when implanted and converted to a denture prosthesis provides for the appearance of natural teeth while being fixed in the jaw, providing aesthetic benefits for an edentulous or partially edentulous patient. Further, the invention may provide for shorter surgery times for implantation of the device as well as greater precision in placement compared to conventional devices. In addition, the device may be converted to a temporary or final prosthesis. The device can be used with a variety of implants for implantation into jaw bone.

BRIEF DESCRIPTION OF THE DRAWINGS

The accompanying drawings illustrate certain aspects of embodiments of the present invention, and should not be used to limit the invention. Together with the written description the drawings serve to explain certain principles of the invention.

FIG. 24 shows guided surgery information for a patient according to an embodiment of the invention.

FIG. 25 shows a treatment planning approval form according to an embodiment of the invention.

FIGS. 28A-28D show a Single Scan Protocol for Teeth-supported Surgical Guide according to an embodiment of the invention.

FIGS. 29A-29E show a Dual Scan Protocol for Teeth-supported Surgical Guide according to an embodiment of the invention.

FIGS. 30A-30F show a Dual Scan Protocol for Gum-Supported Surgical Guide according to an embodiment of the invention.

FIGS. 31A-31D show file transfer instructions according to an embodiment of the invention.

DETAILED DESCRIPTION OF VARIOUS EMBODIMENTS OF THE INVENTION

Figure 1:
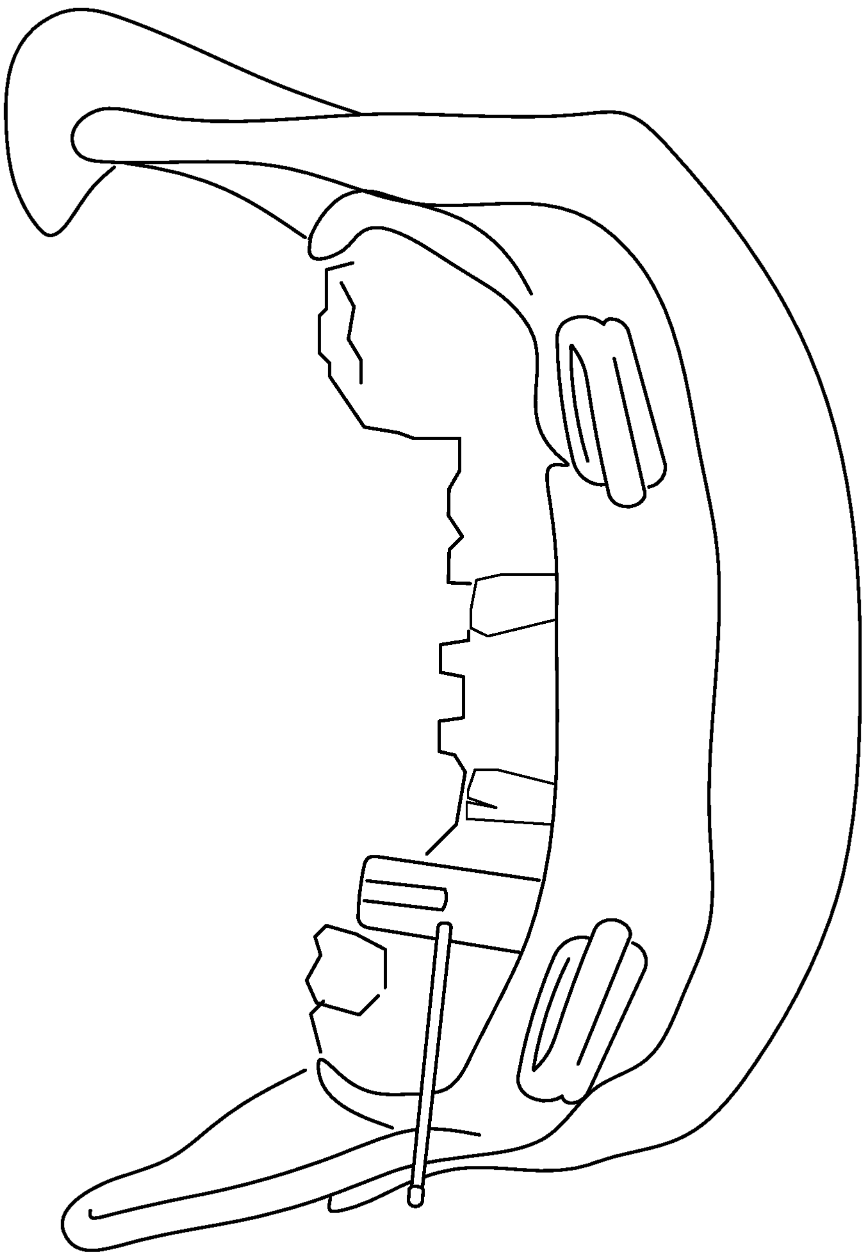
FIG. 1 shows a prior art surgical guide half prosthesis.
Figure 2B:
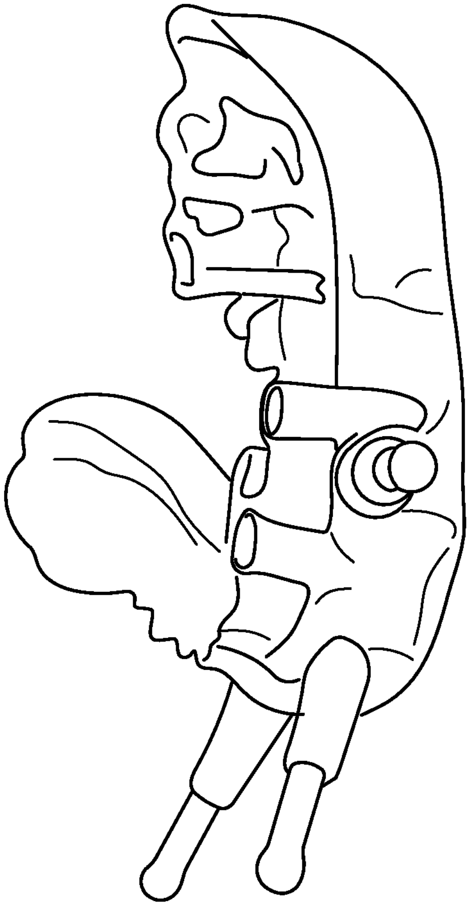
FIG. 2B shows a prior art tooth- and pin-supported PMMA Milled Split Surgical Guide.
Figure 2A:
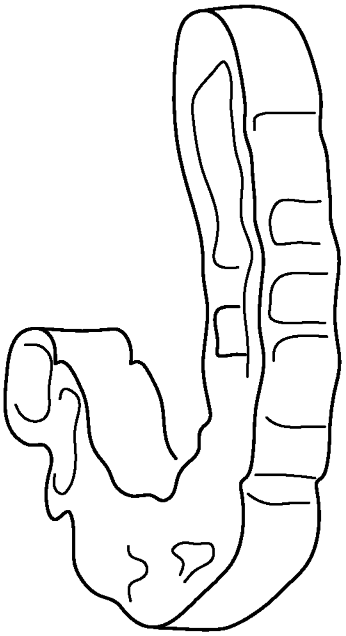
FIG. 2A shows a prior art tooth-supported poly(methyl methacrylate) (PMMA) Milled Split Surgical Guide.

Reference will now be made in detail to various exemplary embodiments of the invention. It is to be understood that the following discussion of exemplary embodiments is not intended as a limitation on the invention. Rather, the following discussion is provided to give the reader a more detailed understanding of certain aspects and features of the invention.

In one embodiment, the present invention is a two-part denture prosthesis or device comprising a surgical template or guide and removable false teeth set for both the mandibular and maxillary jaw. The surgical template and false teeth set may be configured to fit together in an interlocking configuration. The surgical guide may exist as two components that are each configured to fit the top (maxilla) or bottom (mandible) portion of a patient's jaw when placed inside the mouth. The surgical guide may have one or more holes that may serve as drilling sites. The holes may be positioned so that osteotomies may be drilled downward in the mandible or upward in the maxilla. The holes in the guide can comprise a cylindrical wall (also known herein as a depth stop) that is raised or lowered to accommodate a target depth of the osteotomy. The surgical guide may have one or more pin holes for securing or clamping the guide to the jaw during surgery. During surgical placement of the guide, pins can be set through the pin holes in the guide through the bone to secure the guide in place until it is permanently fixed with the abutments or implants. In embodiments, the pin holes are located laterally on the guide and spaced apart to secure the sides and central portion of the guide.

In embodiments, the surgical guide has a removable false teeth set configured to interlock with the surgical guide. The removable teeth may exist as two additional components (e.g., one for the maxillary jaw and one for the mandibular jaw) each configured to fit the top maxillary portion or bottom mandibular portion of the surgical guide. The removable false teeth set allows the oral surgical guide to be simultaneously used as a prosthesis. In addition, the removable false teeth are useful in helping to confirm the fit of the surgical guide through occlusion. The removable teeth may fit on the surgical guide above or below the drill holes and may have access holes that complementarily fit the drill holes. Ultimately, the surgical guide and teeth component are secured as one piece to the implant(s) placed in the jaw though a fastener such as screws.

The surgical guide may be manufactured to fit the individual patient's mouth based on a CT scan of the maxilla and mandible. The surgical guide may be manufactured from a nanoceramic composite or other suitable material through CNC milling or 3D printing.

In another embodiment, the invention is a method for performing oral surgery. The method comprises placing a surgical guide of the invention in a patient's mouth, setting one or more pins through the holes of the guide to secure the guide to the jaw, placing a set of teeth on the guide, instructing the patient to bite down on the teeth to confirm the fit of the guide through occlusion, if necessary, releasing the guide with the pins and readjusting the fit of the guide based on the occlusive bite, and securing the guide with the pins, drilling osteotomies through the holes, and securing the guide to the jaw through implants or abutments placed in the osteotomies. The methods may further comprise using a pre-surgical bite registration index based on the patient's bite. The methods may further comprise cutting off insertion pin holes and flanges on the guide and filling the border between the surgical guide and false teeth set with composite to provide for a natural look.

In another embodiment, the invention is a method of placing a dental prosthesis in the mouth of a patient. The method comprises placing a surgical guide in the mouth of a patient, performing guided surgery based on drill holes in the surgical guide, inserting abutments through the surgical guide, retrieving the surgical guide and reducing excess material, inserting a complementary false teeth set into the surgical guide, drilling a guided screw channel into the surgical guide, and finishing the surgical guide.

Figure 3A:
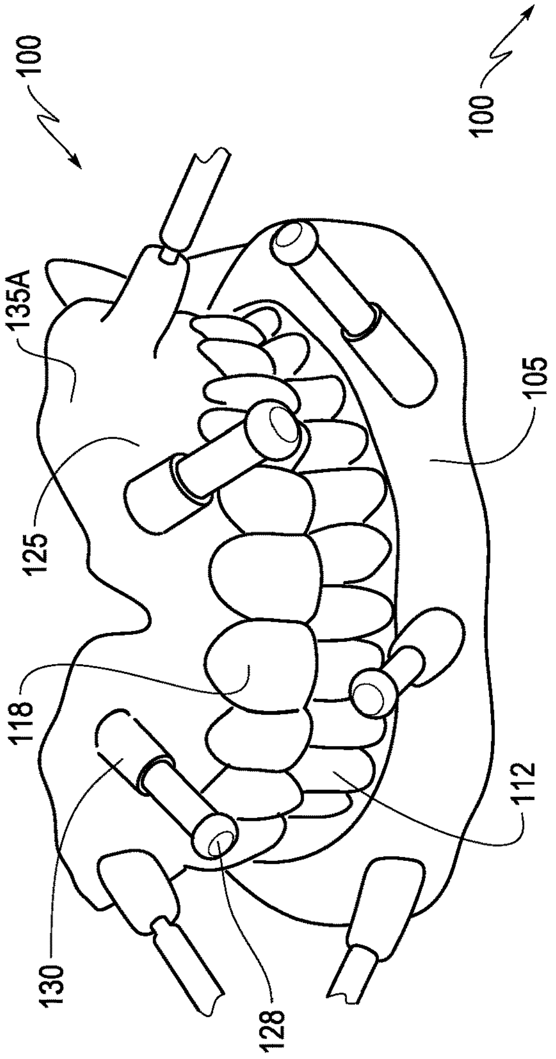
FIG. 3A shows a front View of a fully assembled combination surgical template and dental prosthesis device according to an embodiment of the invention.
Figure 3B:
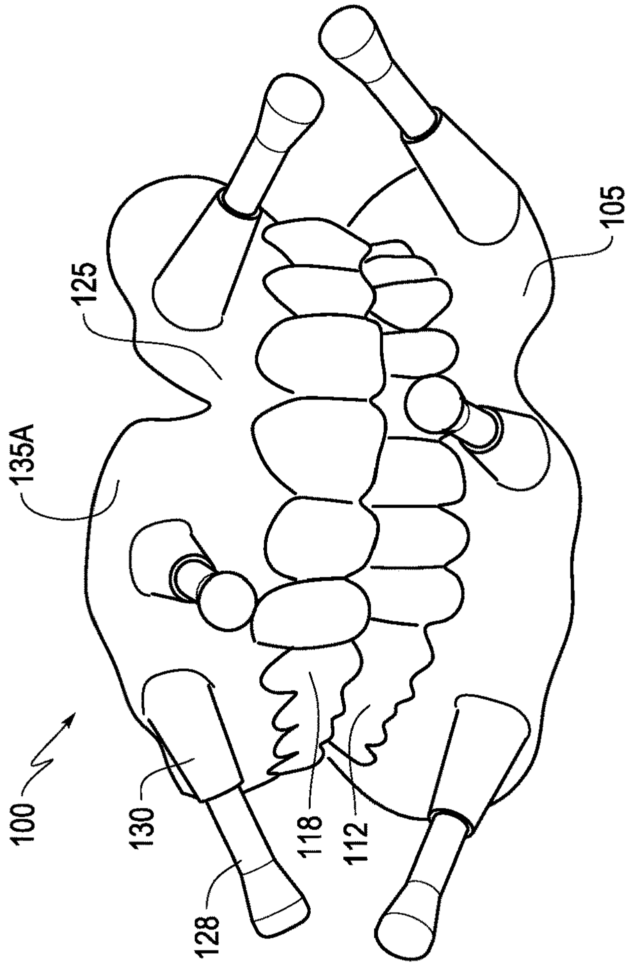
FIG. 3B shows a front, oblique view of a fully assembled combination surgical template and dental prosthesis device according to an embodiment of the invention.
Figure 3C:
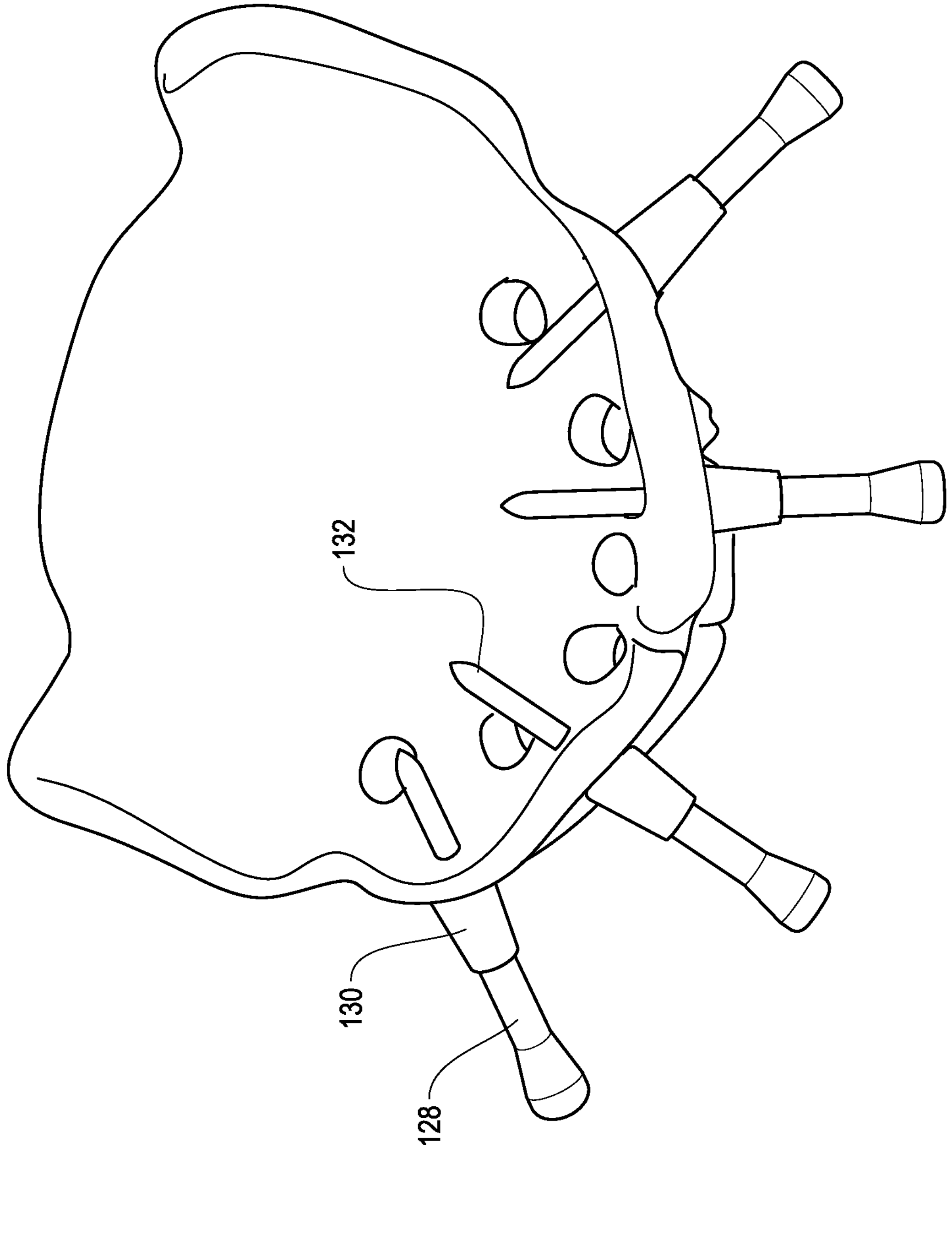
FIG. 3C shows a top view of a maxillary portion of a combination surgical template and dental prosthesis device according to an embodiment of the invention.

Various embodiments of a device of the invention are shown in FIGS. 3-18F. FIGS. 3A-3B show a manufactured/milled denture prosthesis 100 according to an embodiment of the invention. The denture prosthesis includes mandibular guide 105, mandibular false teeth set 112, maxillary guide 125, and maxillary false teeth set 118. Guides 105 and 125 include insertion pin holes 130 and insertion pins 128 as well as flanges 135A extending above the guides. Guides 105, 125 may have portions with the color, shape, and appearance of gum tissue. The insertion pins 128 may be used to pin the guide in position into the jaw bone based on results of the CT scan and holds the guide in place like a vise. The false teeth sets 112 and 118 are used as a reference for orientating the guides 105 and 125 into the jaw during placement. The guide is first preliminarily placed in the mouth based on the results of the CT scan, the teeth are placed in the guide, and the patient's mouth is closed to provide occlusion of the false teeth set with the natural teeth set on the opposite jaw. This method is also called canine guidance, in which occlusal contacts of the cuspids cause contacts of posterior teeth to separate in excursive mandibular movements. Occlusion confirms that the guide is in proper position. The false teeth sets 112 and 125 may be glued to the guides 105 and 125 during final preparation of the dental prosthesis. FIG. 3C shows that insertion pins 128 have a tapered portion 132 projecting inward through and beyond insertion holes 130 for insertion into the jaw.

As will be shown below, the false teeth sets 112, 118 and guides 105, 125 may include features that allow corresponding components to fit into place. These may include at least one male component on the guides 105, 125 and at least one female component on the teeth or vice versa. In one embodiment, the guides 105, 125 have a male component having an appearance of a molar tooth structure that interlocks with a molar tooth structure of the corresponding false teeth sets 112, 118. In other embodiments, the guides 105, 125 have a ledge or gulley that is configured to accept a protruding portion of the corresponding false teeth sets 112, 118. Once they are fit together, false teeth sets 112, 118 and guides 105, 125 may be permanently fixed together through an adhesive such as a composite.

Figure 4:
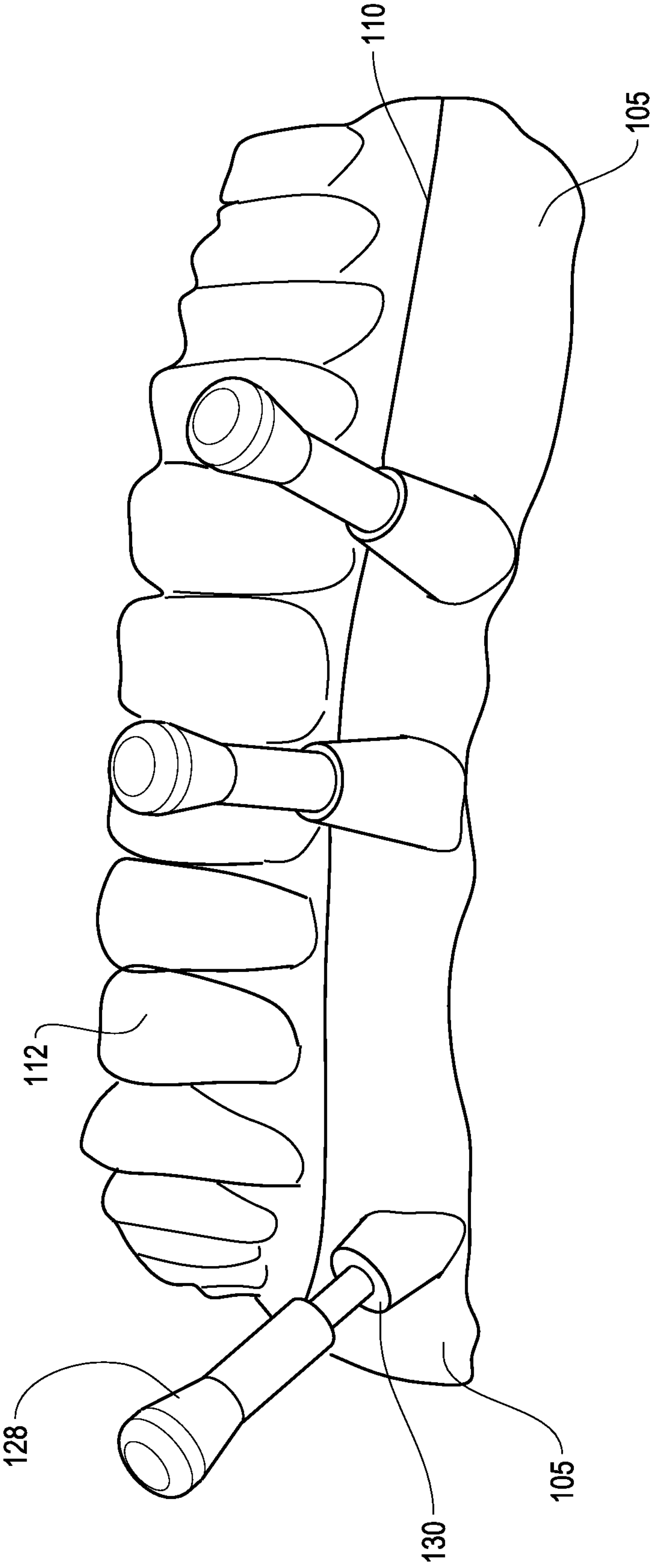
FIG. 4 shows a mandibular portion of a combination surgical guide dental prosthesis device according to an embodiment of the invention.
Figure 5:
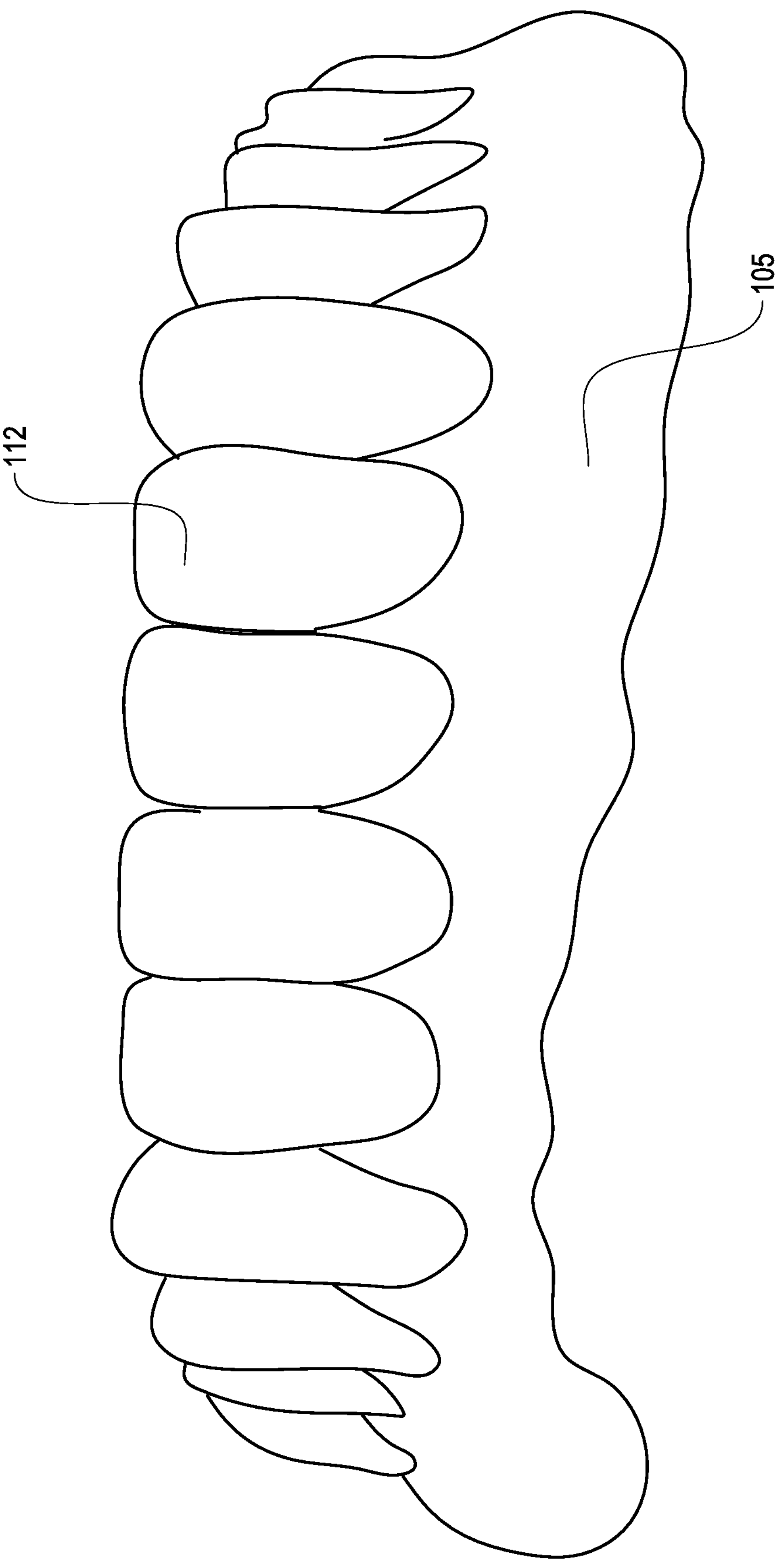
FIG. 5 shows a surgical template converted to dental prosthesis with pins, pin holes, and flanges removed according to an embodiment of the invention.
Figure 6A:
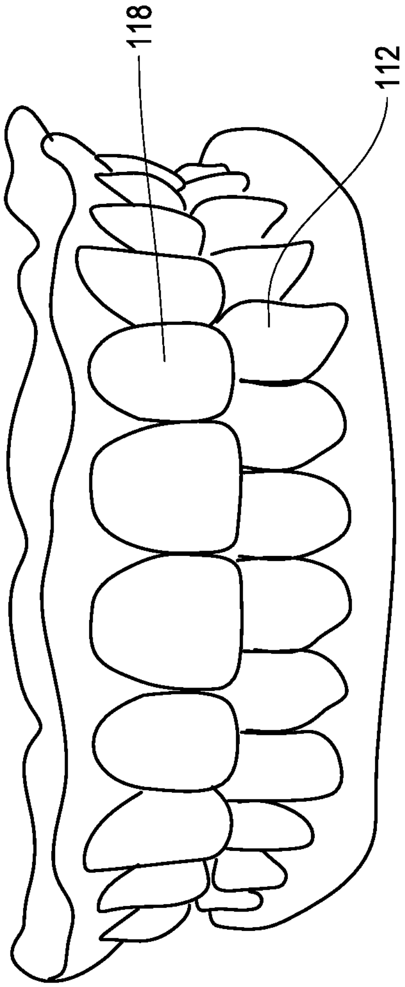
FIG. 6A shows a front view of an embodiment of the surgical template converted to a temporary dental prosthesis with pins, pin holes, and flanges removed according to an embodiment of the invention.
Figure 6B:
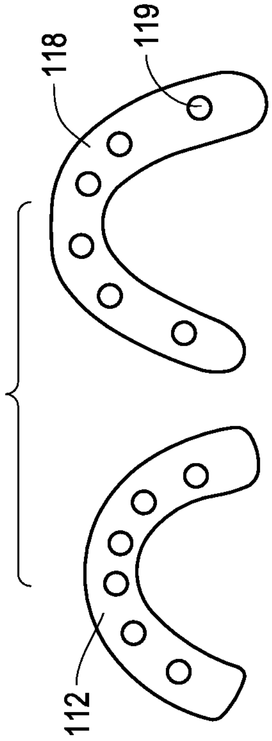
FIG. 6B shows a bottom view of an embodiment of the surgical template converted to a final dental prosthesis showing towers from multi-unit abutments.

FIG. 4 includes a surgical guide 105 and false teeth set 112 which includes line 110 at point of insertion of false teeth set 112 into surgical guide 105. Since the surgical guide 105 and false teeth set 112 will serve as a prosthesis, unnatural features such as insertion pin holes 130 and line 110 must be removed from the device during a conversion process. FIGS. 5 and 6A shows a surgical guide 105 and false teeth set 112 with line between them removed by filling with composite and insertion pin holes removed. The surgical guide 105 and false teeth set 112 shown in FIG. 5 is processed according to how it would appear in a patient. FIG. 6A shows the maxillary 118 and mandibular 112 false teeth sets together in occlusion. FIG. 6B shows a bottom view of an embodiment of the surgical template converted to a final dental prosthesis showing towers 119 from multi-unit abutments.

Figure 7:
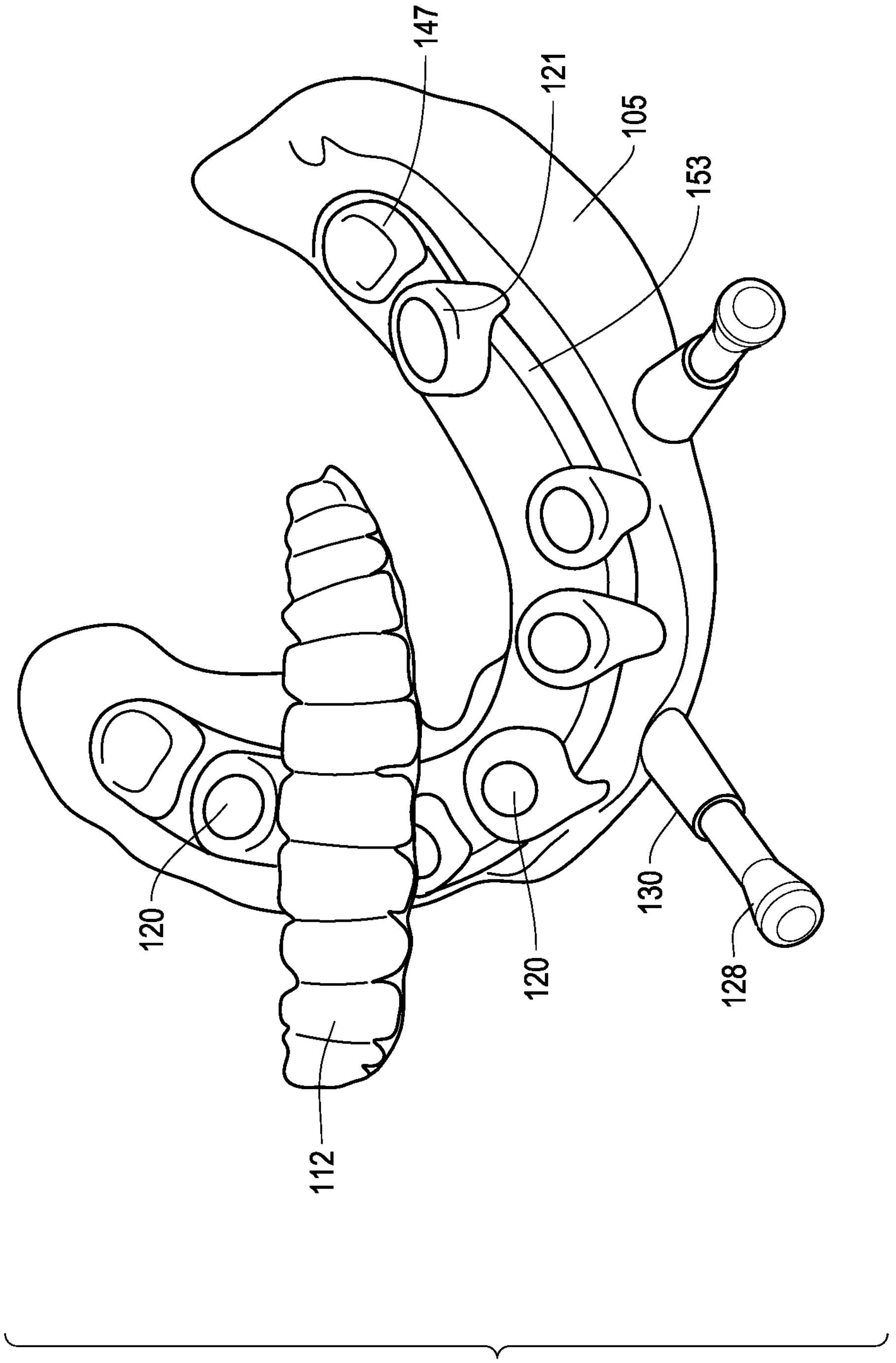
FIG. 7 shows a two-part design of a combination surgical template and dental prosthesis device according to an embodiment of the invention.
Figure 8A:
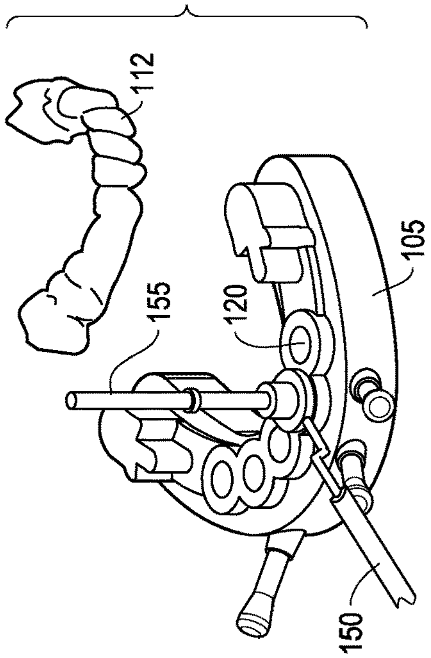
FIG. 8A shows a front, oblique view of a drilling sequence of a combination surgical template and dental prosthesis device according to an embodiment of the invention.
Figure 8C:
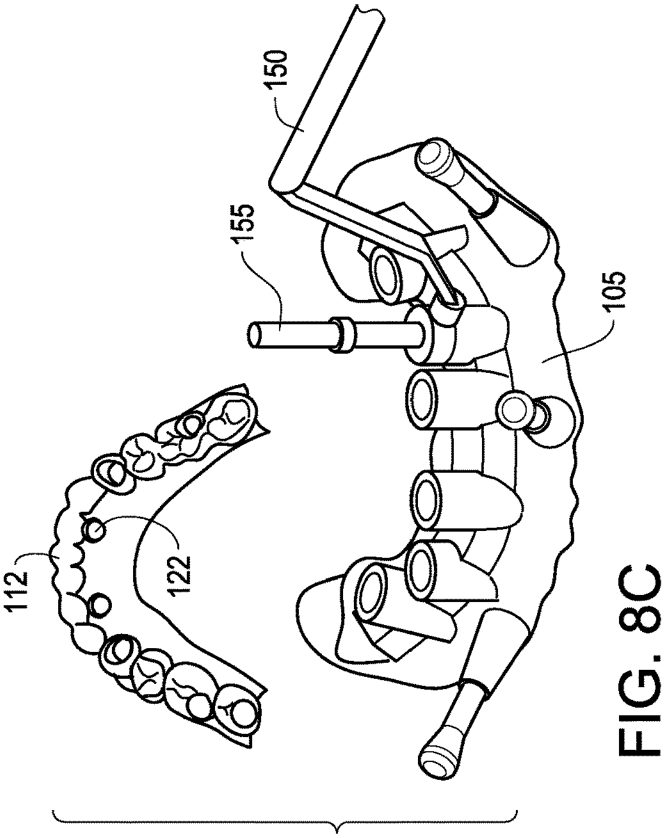
FIG. 8C shows a front view of a drilling sequence of a combination surgical template and dental prosthesis device according to an embodiment of the invention.
Figure 8B:
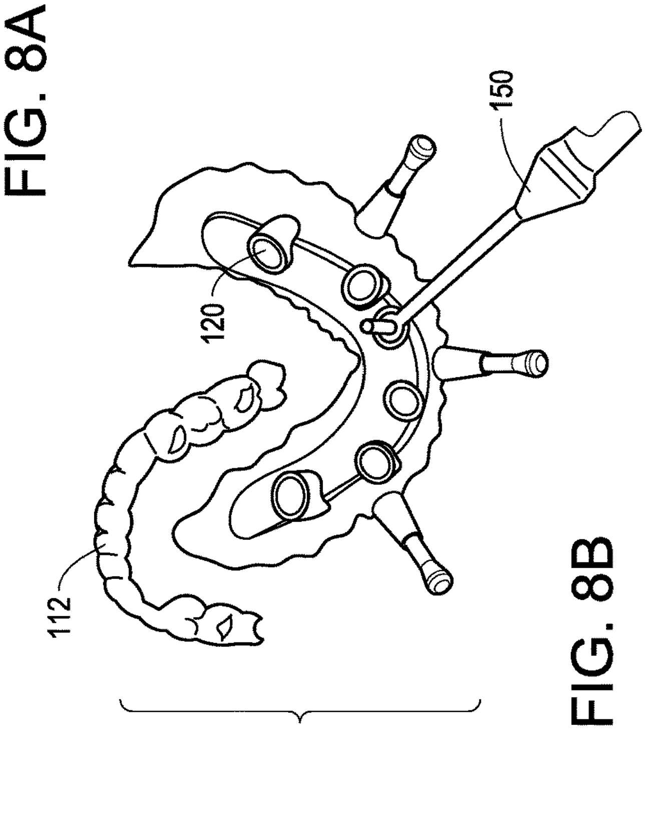
FIG. 8B shows a top view of a drilling sequence of a combination surgical template and dental prosthesis device according to an embodiment of the invention.

Turning now to FIG. 7, shown is a surgical guide 105 with separated false teeth set 112, which reveals drilling sites 120 on the surgical guide 105. The drilling sites 120 comprise a cylindrical hole which may be provided at different depths to help guide the depth of the drill hole. For example, a cylindrical hole may include a wall 121 at a specified height to prevent drilling too deep. These cylindrical hole configurations are also known as depth stops. As shown in FIGS. 8A-8C, the drilling sites 120 may be accessible through guided surgical drilling equipment 150, 155, which may drill osteotomies in the jaw for fixing the surgical guide 105 and false teeth set 112 into the jaw. Also shown in FIG. 8C are complementary holes 122 in the false teeth set which align with the drilling sites 120 which serve as screw access holes.

Figure 9A:
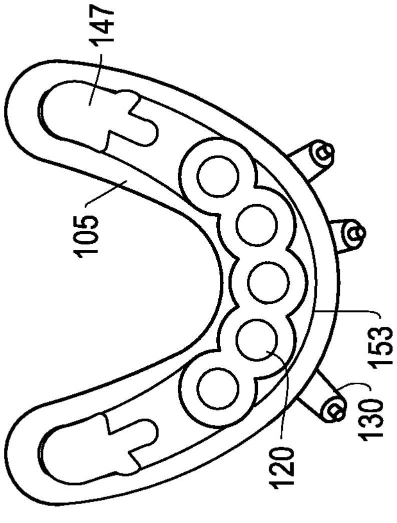
FIGS. 9A-9D show a chair-side adaptation workflow according to an embodiment of the invention.
Figure 9B:
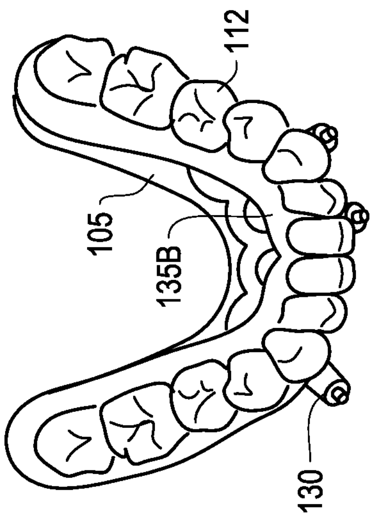
Figure 9C:
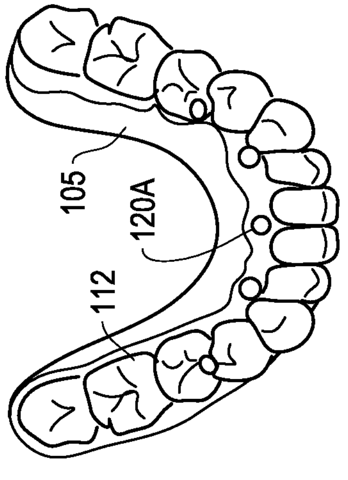
Figure 9D:
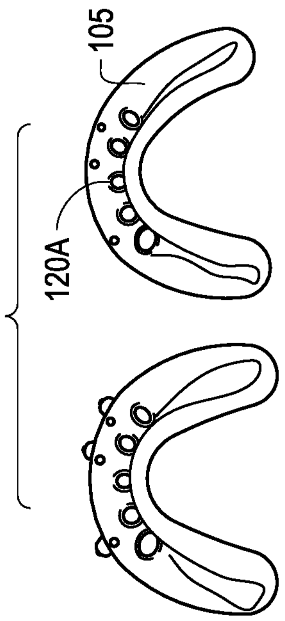
Figure 10B:
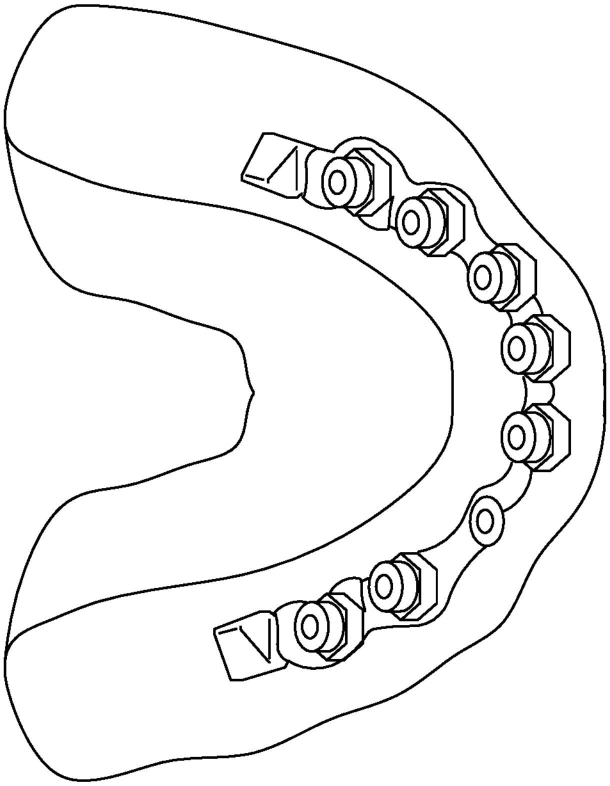
FIG. 10B shows bars embedded in a nanoceramic prosthesis according to an embodiment of the invention.
Figure 10A:
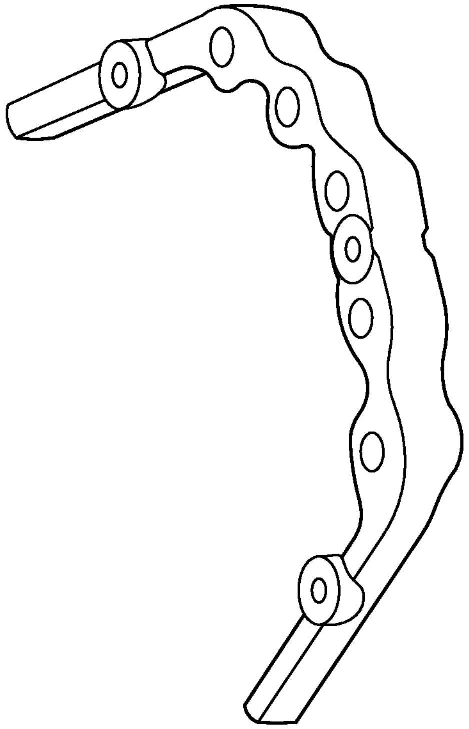
FIG. 10A shows bars milled for final clone prosthesis according to an embodiment of the invention.

Now referring to FIGS. 9A-9D, shown are a surgical guide and dental prosthesis device of the invention at different stages of assembly. FIG. 9A shows a mandibular surgical guide 105 with the removable false teeth set 112 removed, while FIG. 9B shows the mandibular surgical guide 105 with the removable false teeth set 112 attached. Also shown in FIGS. 7 and 9A are interlocking structure 147 and horseshoe-shaped ledge 153 for connecting false teeth set 112 to mandibular surgical guide 105. Such features may be used to fit the two components in place. FIGS. 9C and 9D show the surgical guide 105 with excess material removed, including the interior drilling sites 120A, flange 135B, and insertion pin holes 130 shown in FIGS. 9A and 9B. In embodiments, the excessive material reduction is a component of a Chair-Side Adaptation Workflow, which includes the following steps:

1. Guided surgery
2. Abutment (not shown) insertion and bonding, through surgical guide still installed
3. Surgical guide retrieval and excess material reduction
4. Surgical guide parts assembly and bonding
5. Guided screw channel drilling
6. Finishing In embodiments, the device of the invention may be used as a temporary prosthesis until a more permanent prosthesis is put into place. FIGS. 10A and 10B show the manufacture of a more permanent prosthesis based on the device. FIG. 10A shows bars milled for final clone prosthesis according to an embodiment of the invention. FIG. 10B shows bars embedded within a nanoceramic prosthesis according to an embodiment of the invention. The more permanent prosthesis may be implanted in the jaw through the implants installed through the surgical guide.

Figure 11A:
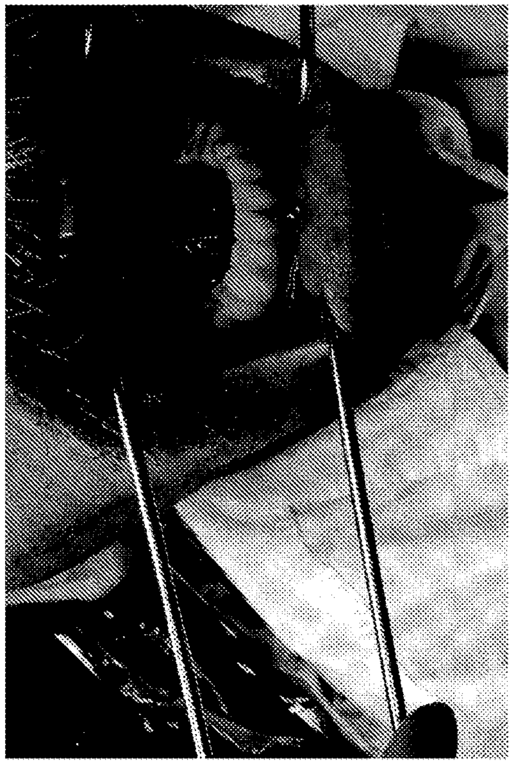
FIG. 11A is a photograph showing a front view of a patient implanted with a converted surgical guide and dental prosthesis device according to an embodiment of the invention.
Figure 11B:
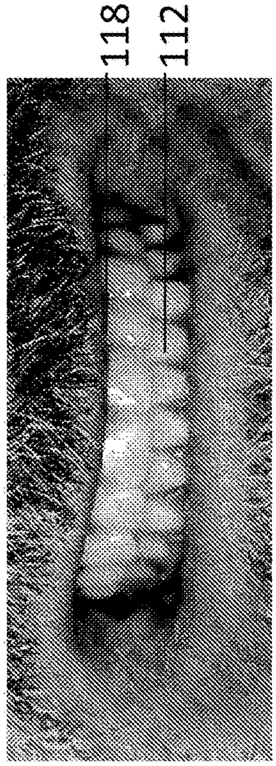
FIG. 11B is a photograph showing a front view of a patient implanted with a converted surgical template and dental prosthesis device according to an embodiment of the invention with teeth in occlusion.
Figure 11C:
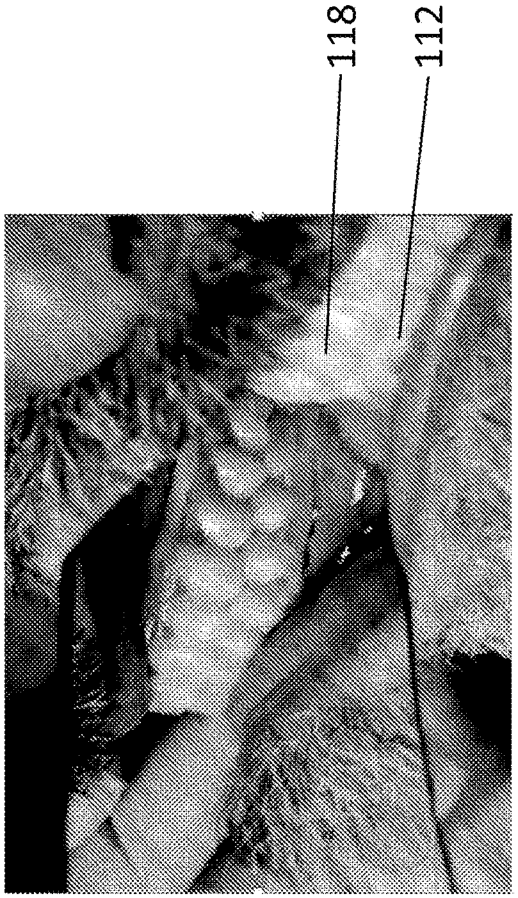
FIG. 11C is a photograph showing a side view of a patient implanted with a converted surgical template and dental prosthesis device according to an embodiment of the invention with teeth in occlusion.

FIGS. 11A-11C show a patient implanted with a surgical guide converted to a dental prosthesis according to an embodiment of the invention. As shown in FIGS. 11B and 11C, the maxillary 118 and mandibular 112 false teeth sets are positioned so that they are in perfect occlusion with canine guidance.

In embodiments, the surgical guide may include one or more retaining pins and drill holes located on the denture which serve as a surgical guide for bone reduction. The bone reduction guide assists the user to reduce bone to the necessary thickness in order for the denture to be placed at the right height, and may be determined from a CT scan of the patient's jaw. The retaining pins and drill holes allow for a boundary on the jaw to be marked when the surgical guide is placed in the jaw as the jaw may be marked by drilling though the drill holes. When the guide is placed the jaw may be exposed through an open flap incision, allowing the oral surgeon to see the holes. The jaw may be reduced by sawing down the jaw until the holes are no longer visible.

Figure 12:
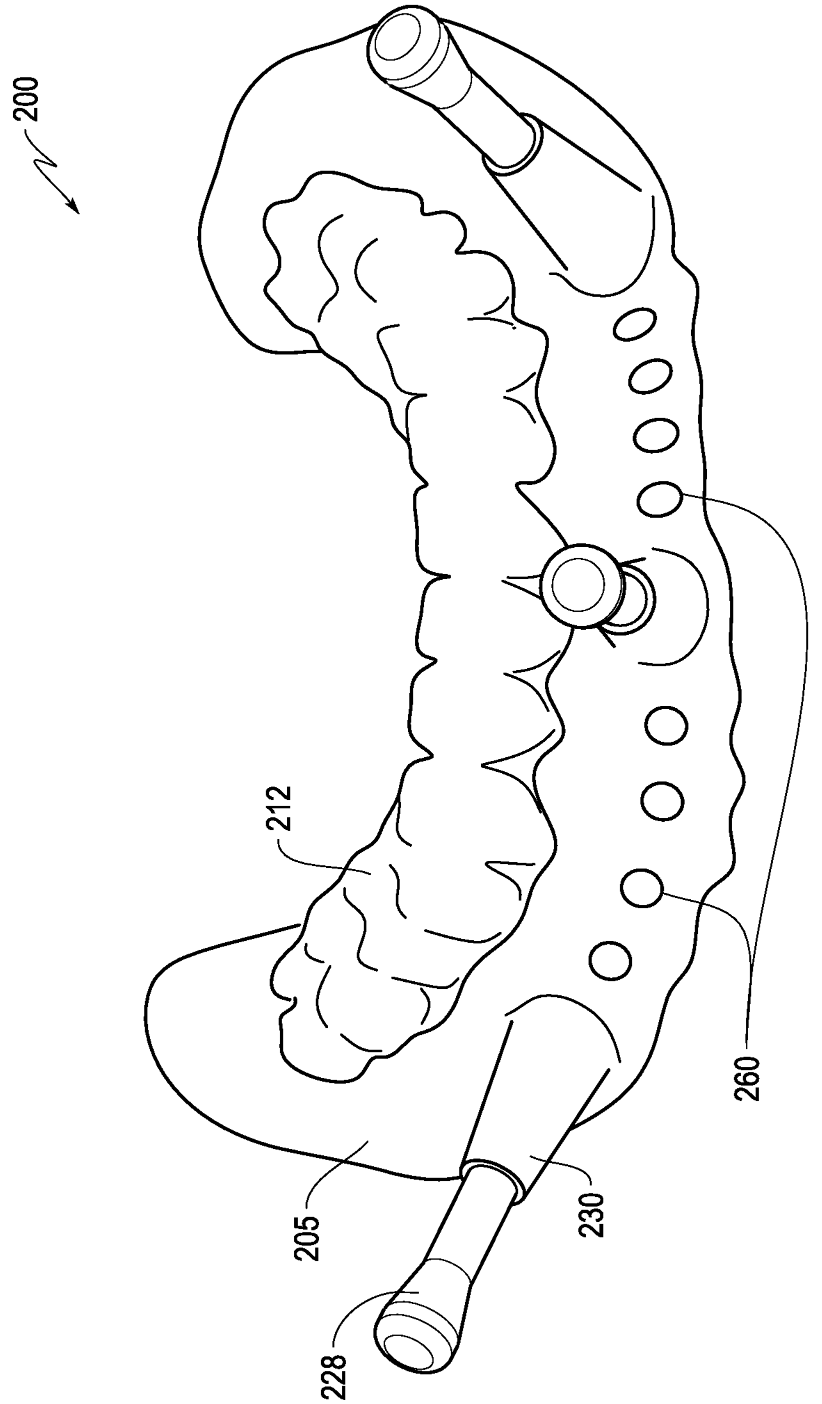
FIG. 12 shows a combination surgical template and dental prosthesis device with bone reduction guide according to an embodiment of the invention.

Now referring to FIG. 12, a partial denture prosthesis 200 comprising a surgical guide 205 with bone reduction guide according to an embodiment of the invention is shown. FIG. 12 shows three retaining pins 228 located in insertion pin holes 230 and two sets of four bore holes 260 located on surgical guide 205, which like previous embodiments has corresponding false teeth set 212. The bore holes 260 are drilled into the surgical guide 205, which provides a bone reduction guide for the device. It acts as a part of the same medical device. The bone reduction guide assists the user to reduce bone to the necessary thickness which may be 15-16 millimeters thick in order for the denture to be placed at the right height. The surgical guide will be stacked on the bone much like a LEGO toy set. The ridge width acts as a guide to remove the bone. The user will push through the tissue and make holes in the bone. Pins inserted into the tissue will be cut. The gum tissue will be opened up and the bone will be exposed. When this happens there will be holes in the bone. The bone will be grinded until the holes disappear at which point the bone will be leveled down along the peak of the mountain peak which is the front or anterior end of the jaw. The surgeon will remove bone along the holes. There will be depressions in the bone and the bone will be ground down until there is a flat plane. The osteotomy is CT driven and will use a denture wherein it will be filled with resin. A denture will be used to get inside of bone. It acts as a surgical guide, prosthesis, and denture guide.

Figure 13:
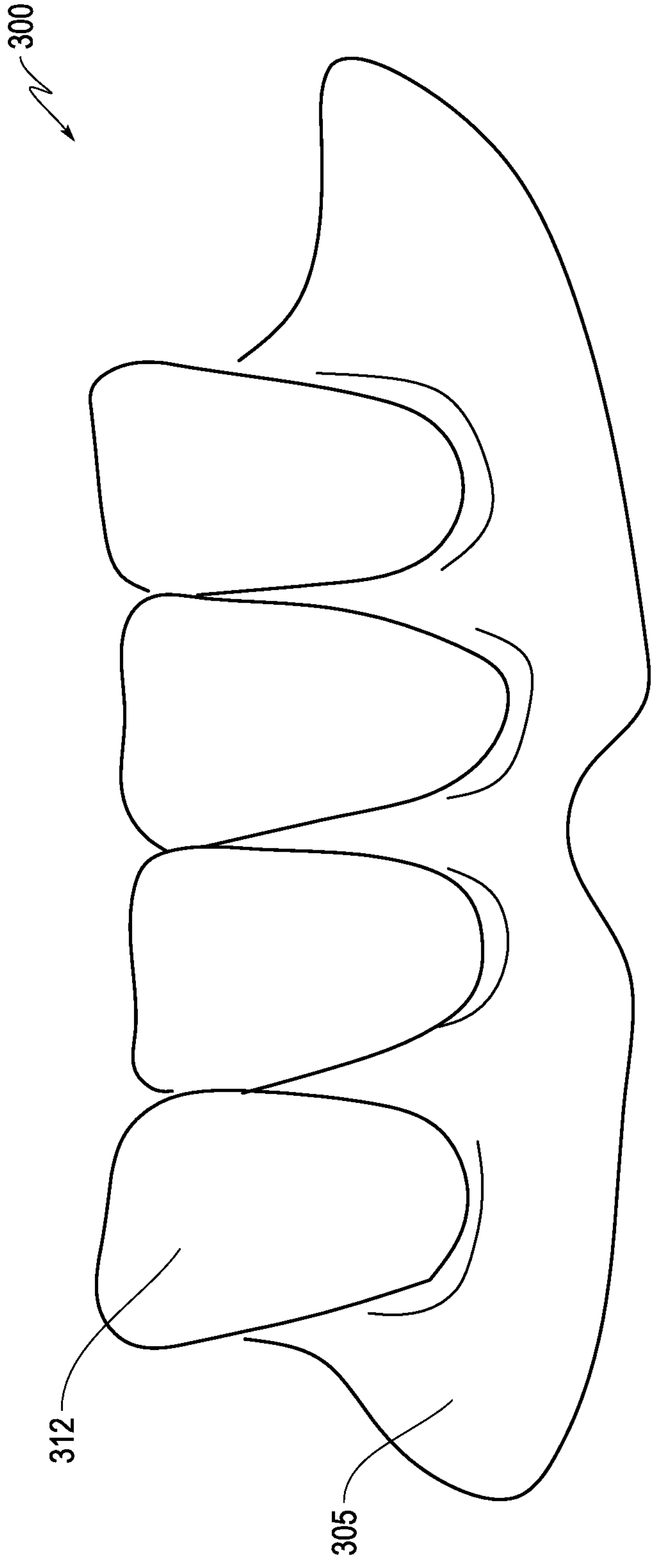
FIG. 13 shows a partial surgical template and dental prosthesis device according to an embodiment of the invention.
Figure 14:
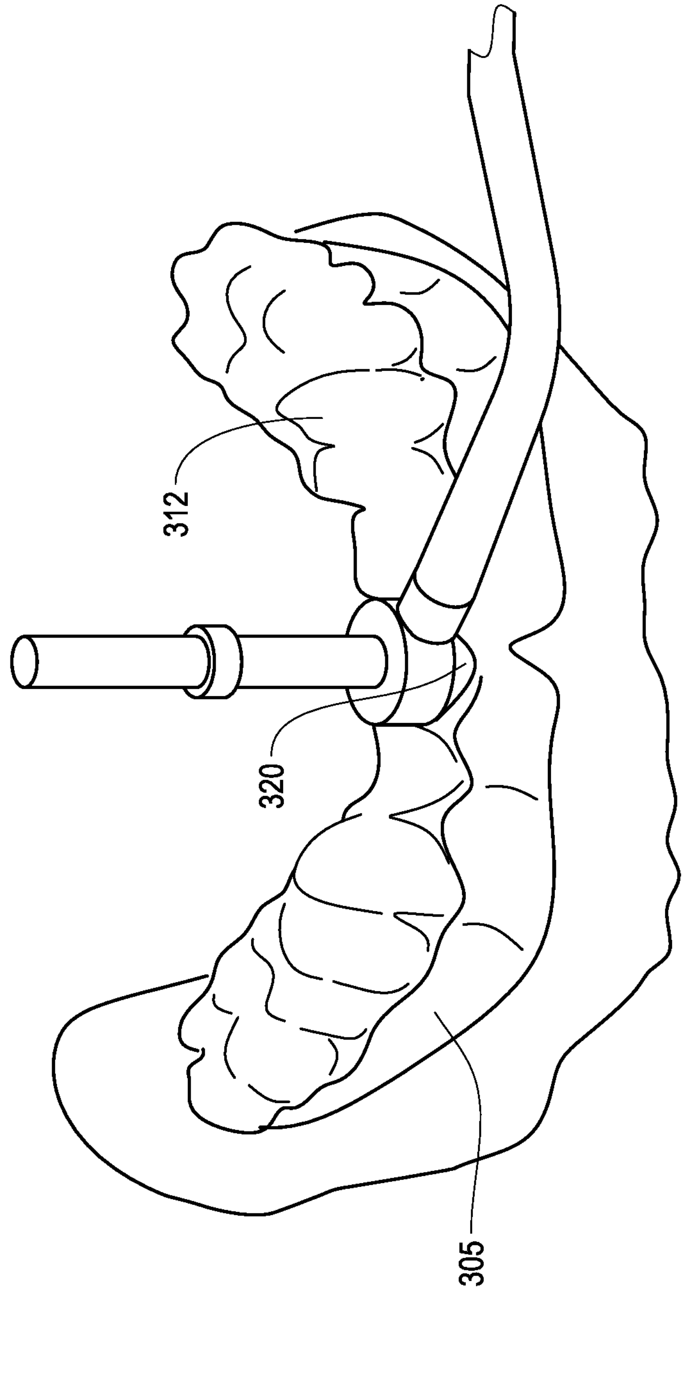
FIG. 14 shows a front view of a drilling sequence of a partial surgical template and dental prosthesis device according to an embodiment of the invention.
Figure 15B:
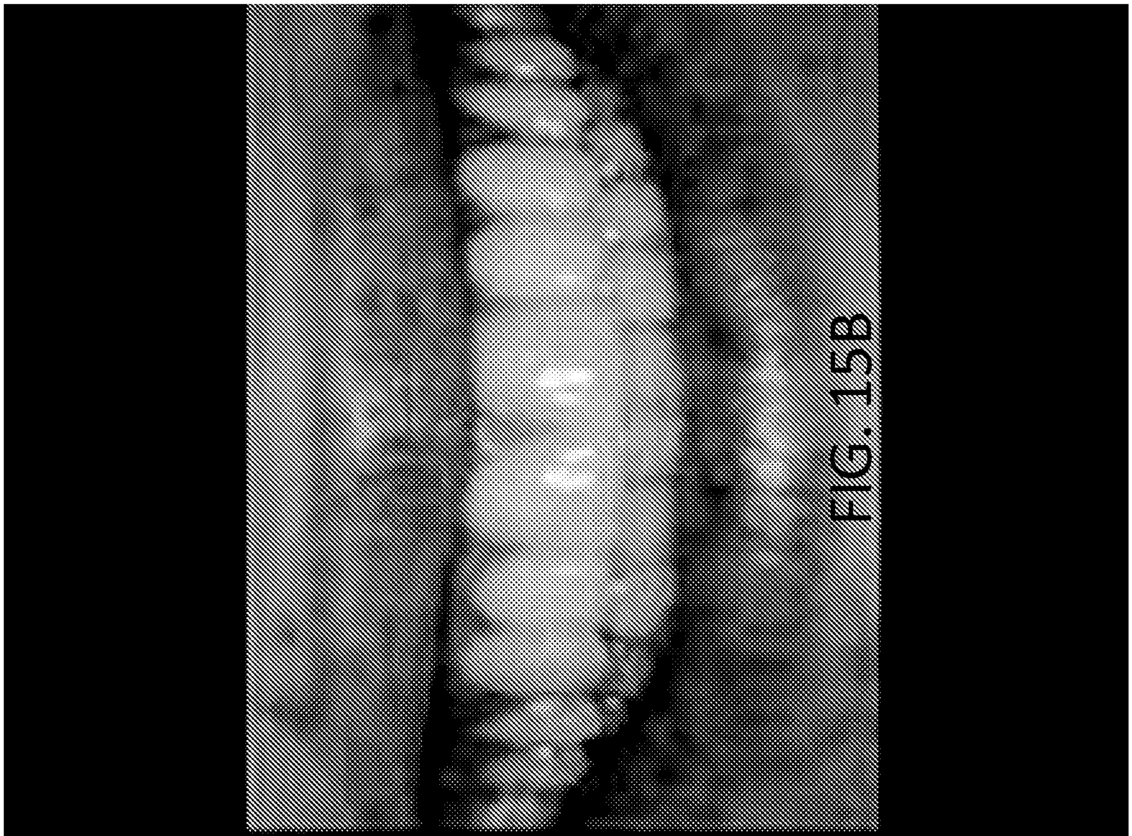
FIG. 15A-15B are photographs before (FIG. 15A) and after (FIG. 15B) of a patient implanted with a partial surgical template and dental prosthesis device according to an embodiment of the invention.
Figure 15A:
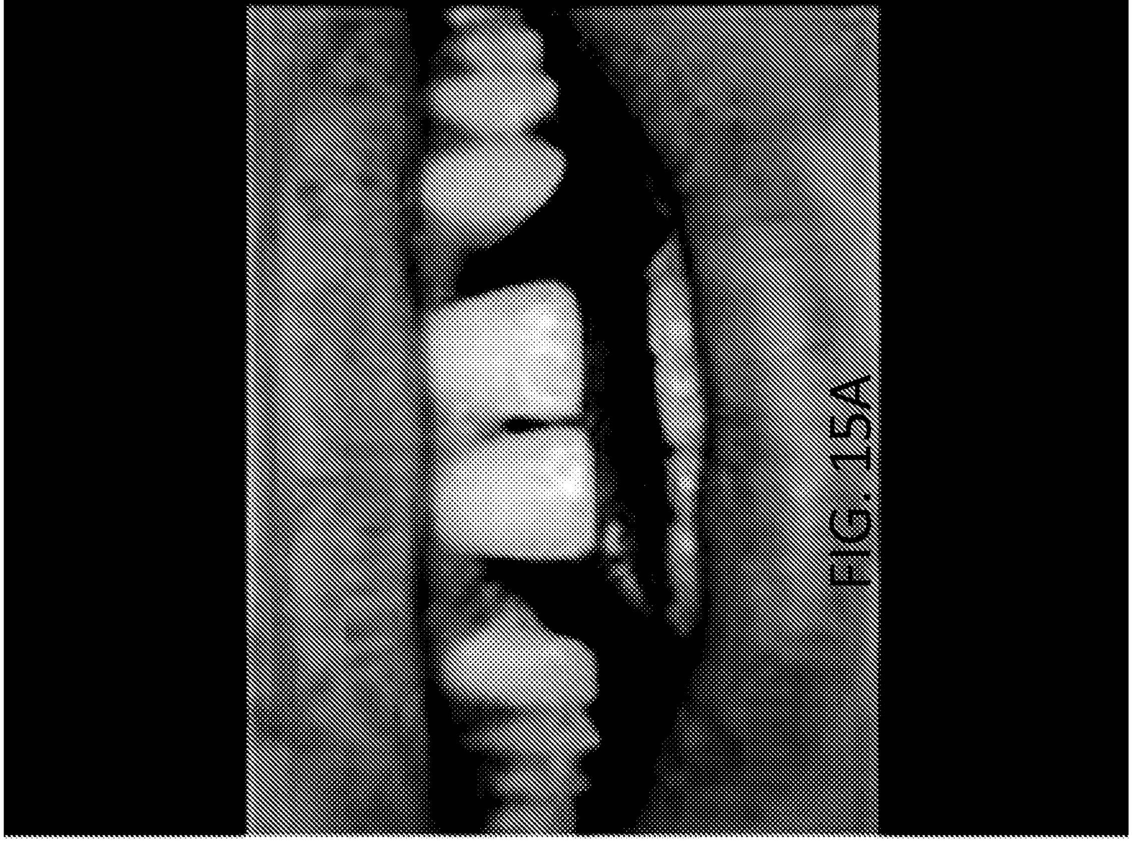

FIGS. 13 and 14 show a partial denture prosthesis embodiment 300 according to the invention. Partial denture 300 includes surgical guide 305 and removable false teeth set 312. When teeth 312 are removed they reveal drill holes 320 which are accessed by drilling equipment. FIGS. 15A and 15B show before after photographs of a patient surgically implanted with the partial denture 300. In embodiments, the partial denture comprises a false teeth set having anywhere from 2 to 8 teeth.

As shown in FIGS. 13 and 14, a surgical guide or template 305 is configured to fit over the gum tissue of a partially edentulous jaw missing one or more incisors. The surgical template 305 has one or more openings 320 each providing a channel for drilling an osteotomy into the maxillary or mandibular jaw at the site of the missing incisors. Included are one or more removable false teeth 312 configured to fit the surgical template at each opening 320. As shown in FIGS. 14, 15A, and 15B, the surgical template and one or more removable false teeth provide a partial or complete bridge between the left and right cuspids when implanted into a patient's jaw. In embodiments, the surgical template is configured to partially wrap around the left and right cuspids to secure it to the jaw.

Figure 16:
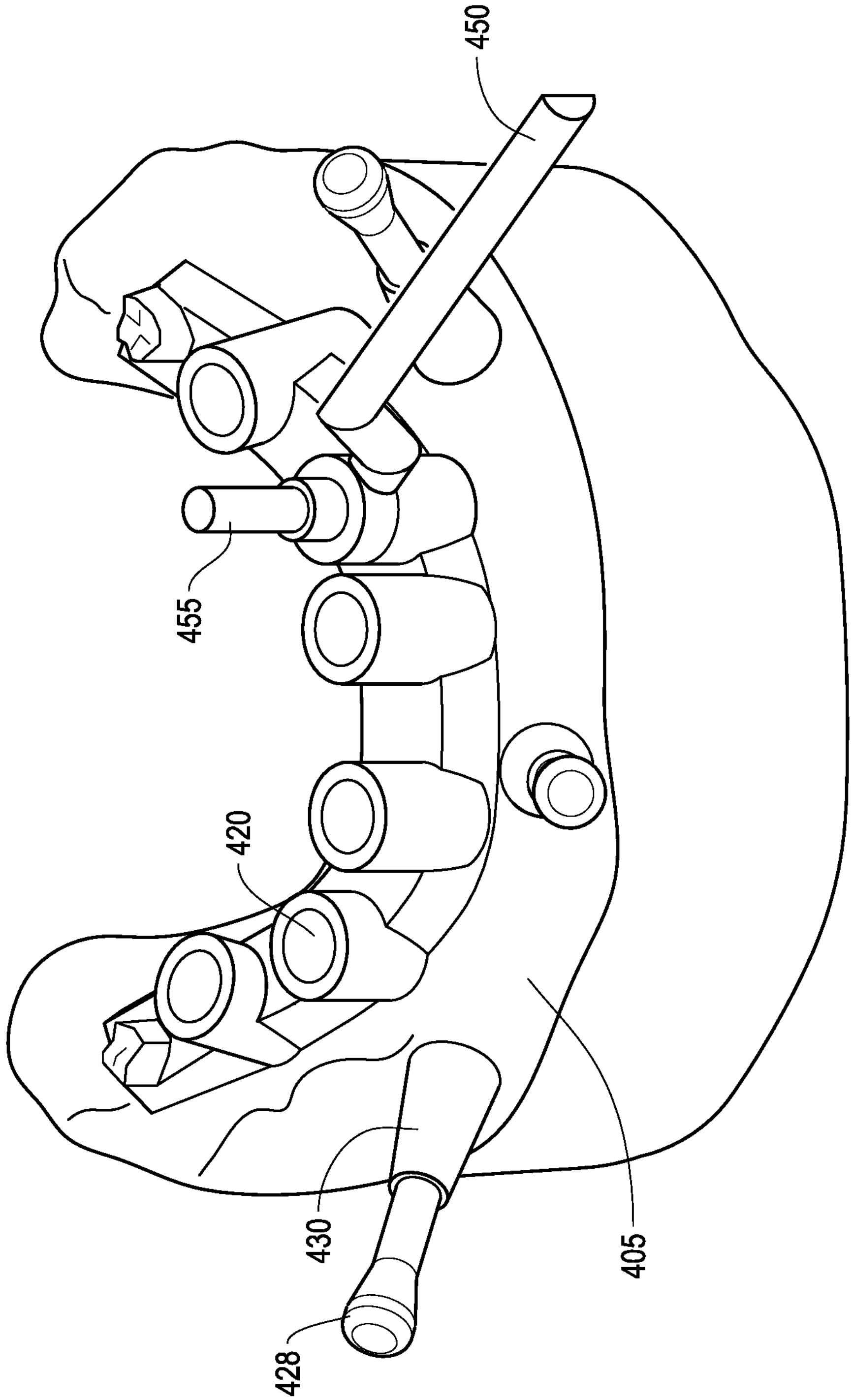
FIGS. 16-17 are drawings showing the combination surgical template and dental prosthesis device of the invention is fully compatible with the BIOHORIZONS® Guided Surgery Kit according to an embodiment of the invention.
Figure 17:
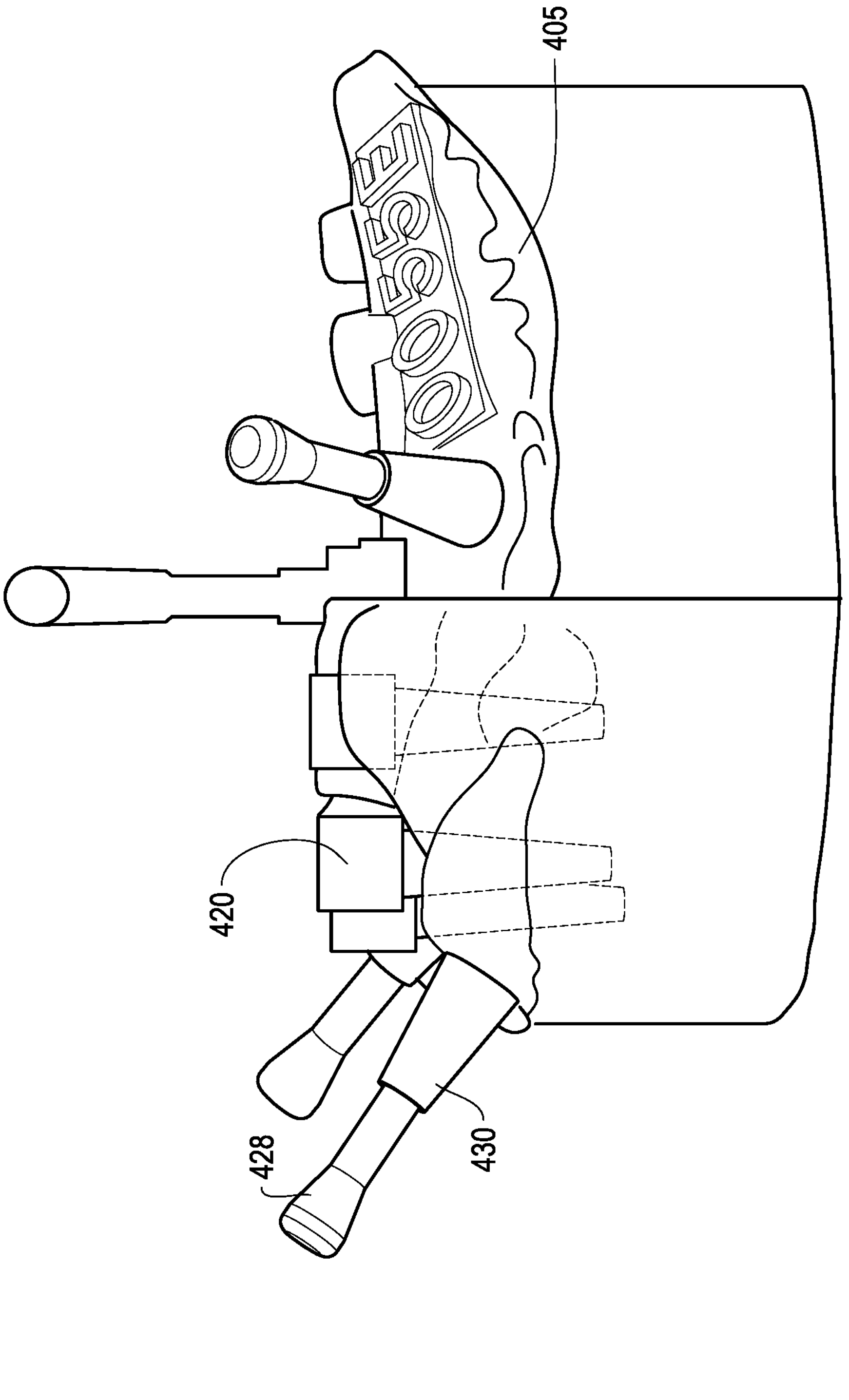
Figure 18A:
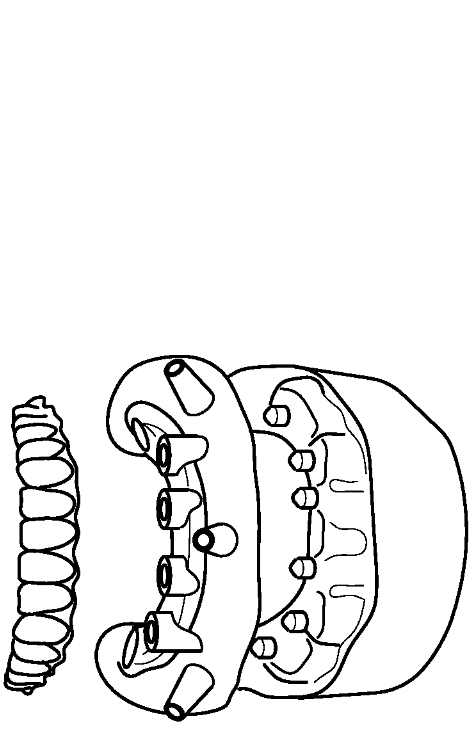
FIGS. 18A-F are drawings showing a series of steps for using a surgical template of the invention with the TEETHXPRESS® immediate load solution according to an embodiment of the invention.
Figure 18B:
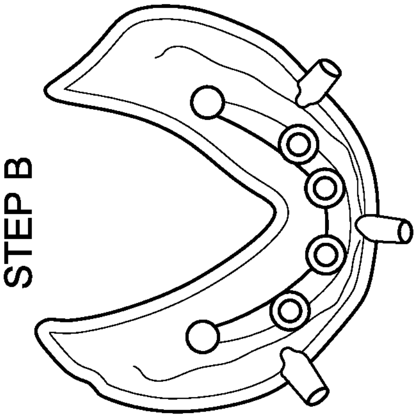
Figure 18C:
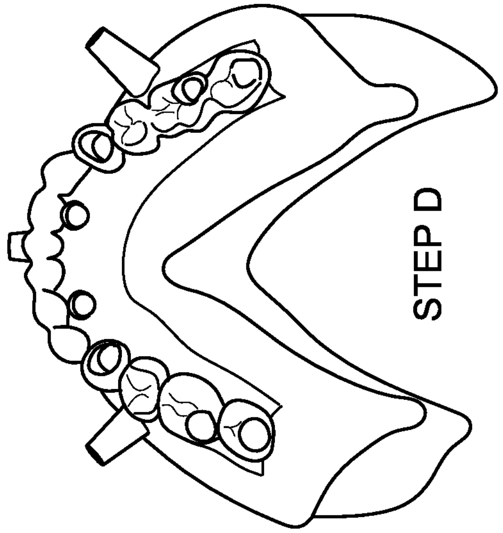
Figure 18D:
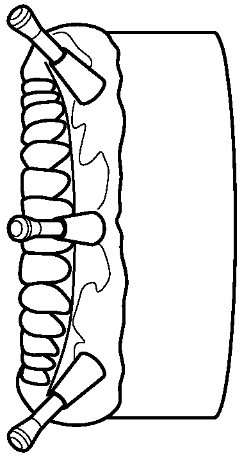
Figure 18F:
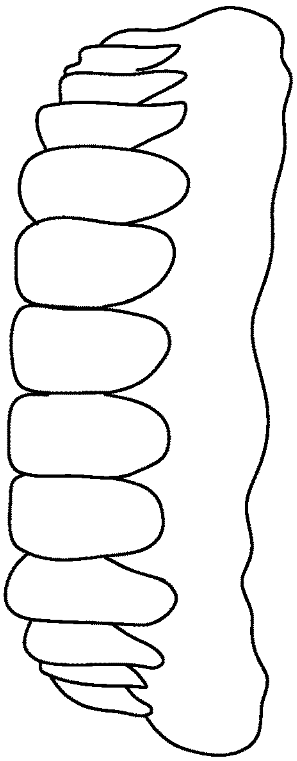
Figure 18E:
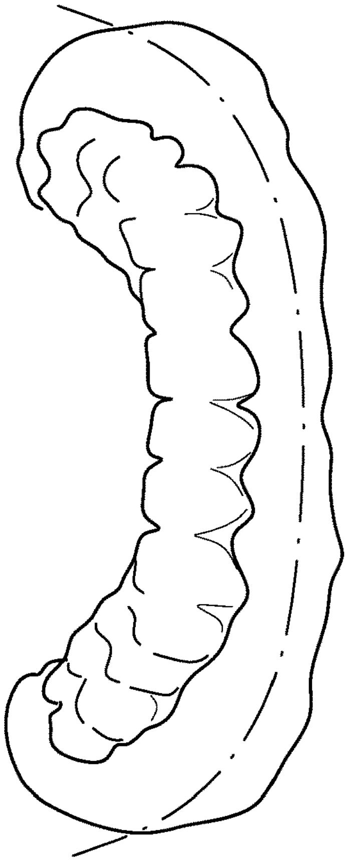

FIGS. 16-17 are CAD drawings showing the surgical guide of the invention is fully compatible with the BIOHORIZONS® Guided Surgery Kit according to an embodiment of the invention. FIGS. 16-17 show guide 405 with insertion pins 428 and insertion pin holes 430, and drilling holes 420 which are accessible by drilling equipment 450, 455. Features of the surgical guide include anchoring using the CGS-FP Fixation pins, secure tool assembly using the embedded pilot drill sleeves or yellow, green and blue Master Cylinders, site preparation using the GGS-YTP/GTP/BTP Tissue Punches, guided osteotomy using BIOHORIZONS® Drill Guides and Drills, all displayed during design to prevent interference with adjacent geometry, guided insertion using the BIOHORIZONS® Implant Drivers and Depth Stops. The four depth stop configurations can be considered during treatment planning.

The following provides specifications of a Demo Case:

Master cylinder=Green

Drill guide=Green, 4.1 mm internal diameter (final)

Implant=4.6 mm×10.5 mm Tapered

Internal Implant=Drill 21 mm length, 4.1 mm diameter (final)

Implant driver and depth position=Tapered Internal 4.6, SP2

FIGS. 18A-F are CAD drawings showing a series of steps for using the surgical guide of the invention with the TEETHXPRESS® immediate load solution according to an embodiment of the invention. Such steps are explained in Table 1 below.

TABLE 1

| Compatibility with TEETHXPRESS ® | | | |
|---|---|---|---|
| Steps | TEETHXPRESS ® | TEETHXPRESS ® + Surgical Guide | Corresponding Figures |
| A. Starting conditions: | Implants with adequate primary stability and proper abutments installed Denture | Implants with adequate primary stability and proper abutments installed Surgical Guide | FIG. 18A |
| B. Initial modifications: | Preparation of a denture hole drilling template Drilling and adjustment of the holes to accommodate the abutments (Steps 1 to 3) | Prefabricated holes aligned according to the treatment plan (with the implants on the baseplate, and with the angled multiunit abutment on the halfprosthesis) Slight adjustments of the holes to accommodate the abutments and copings | FIG. 18B |
| C. Occlusion and passive fit verification: | Using the pre-surgical bite registration index (Step 4) | Using the half-prosthesis, and a pre-surgical bite registration index for cases with challenging prosthetic geometry | |

TABLE 1-continued

| Compatibility with TEETHXPRESS ® | | | |
|---|---|---|---|
| Steps | TEETHXPRESS ® | TEETHXPRESS ® + Surgical Guide | Corresponding Figures |
| D. Coping reduction and installation: | Coping installation, marking, trimming, smoothing, polishing and installation with rubber dam (Steps 5 to 11) | Trim any protruding drill guide supporting cylinders from the baseplate Coping installation, marking, trimming, smoothing, polishing and installation with rubber dam | FIG. 18C |
| E. Occlusion and intercuspation verification: | Using the pre-surgical bite registration index (Step 12) | Using the half-prosthesis, and a pre-surgical bite registration index for cases with challenging prosthetic geometry | |
| F: Coping pick-up: | Using self curing acrylic Using the pre-surgical bite registration index for stability during acrylic curing (Steps 13 to 17) | Using chairside flowable, lightcurable composite Using the Surgical Guide anchor pins for accuracy and stability during composite curing | FIG. 18D |
| G. Prosthesis adaptation: | Retrieve the prosthesis Fill-in any void around the abutments/copings with acrylic Shorten flanges and any excessive posterior cantilever Creation of a 2 mm incision from the mucosa (Steps 18 to 20) | Retrieve the prosthesis Trim the lot number and guide anchors Assemble the half-prosthesis to the base-plate with composite Fill-in any void with composite Shorten flanges and any excessive posterior cantilever Creation of a 2 mm incision from the mucosa | FIG. 18E |
| H. Occlusion verification, polishing and delivery of the prosthesis: | Using the pre-surgical bite registration index Cotton filling and sealing of the screw access holes Acquisition of a post-delivery panoramic x-ray to validate the seating of the prosthesis (Steps 21 to 24) | Using the half-prosthesis, and a pre-surgical bite registration index for cases with challenging prosthetic geometry Cotton filling and sealing of the screw access holes Acquisition of a post-delivery panoramic x-ray to validate the seating of the prosthesis. | FIG. 18F |

Figure 19B:
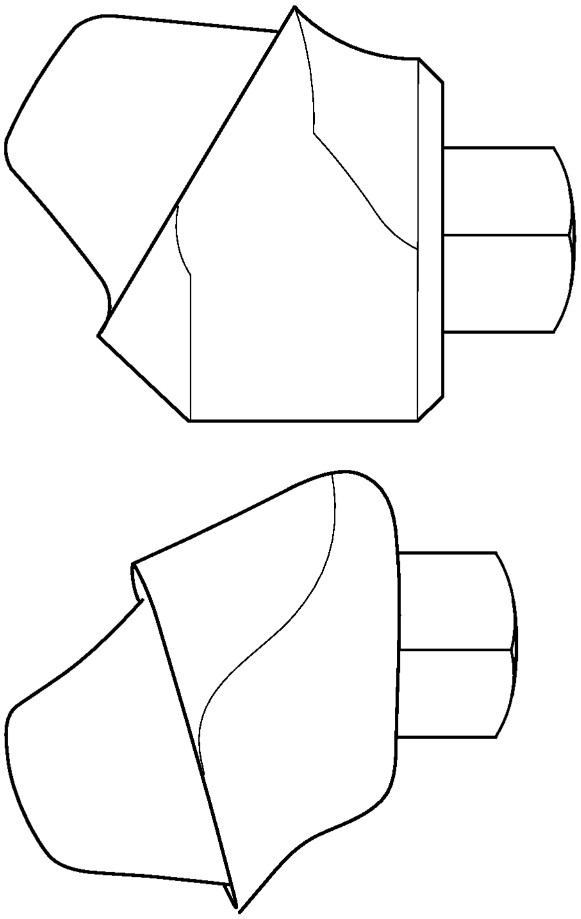
FIG. 19B is a drawing showing an example of BIOHORIZONS® multiunit abutments according to an embodiment of the invention.
Figure 19A:
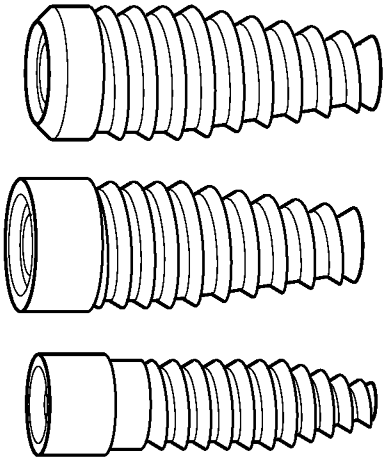
FIG. 19A is a drawing showing an example of BIOHORIZONS® implants according to an embodiment of the invention.

FIG. 19A is a CAD drawing showing an example of BIOHORIZONS® implants according to an embodiment of the invention. FIG. 19B is a CAD drawing showing an example of BIOHORIZONS® multiunit abutments according to an embodiment of the invention. These are examples of implants and abutments that can be used to secure the surgical template of the invention to the jaw. However, the device of the invention is compatible with a variety of implants such that the surgical template may be considered a universal guide.

In another embodiment, the present invention is a method of creating a two-part dental prosthesis comprising a surgical guide and false teeth set. The method comprises performing a CT scan on a patient, transferring the scan (such as in the form of a Digital Imaging and Communications in Medicine (DICOM) file) into treatment planning software. The CT scan slices implant or anchor sites by size and diameter per zone into the jaw bone. From the CT scan, a surgical guide is created based on one or more anchor or implant sites to create a surgical template. The surgical guide may be created by a trained biomedical engineer or oral surgeon who virtually places the implants in position on the CT scan, taking into account the bone quality and quantity and the presence of nerves. The surgical guide is then milled based on the template that provides one or more holes that may serve as drilling sites to place the implants which secure the guide into the jawbone. The drilling sites are created so that the implants are placed at consistent angles to provide for an even pressure distribution on the surgical guide when it is secured in the jaw. A treatment protocol may also be produced from the treatment planning software which instructs a dental surgeon how to place the surgical guide, including the drilling depth. Based on the CT scan, sites in the jaw bone may be identified that may be used to secure one or more implants. The implants may provide a means for securing the device in place with a fastener such as a screw. The device may be attached to the jaw through the implants according to the implant manufacturer's instructions.

In embodiments, the CT scan may be performed in a variety of ways, depending on whether the jaw is fully or partially edentulous and whether metal restorations or amalgams are present. For a partially edentulous jaw, if there is good teeth support, and no metal restorations or amalgams, then the CT scan may be performed without a radiographic guide. If there is good teeth support and amalgams or metal restorations are present, then the CT scan may be performed with a radiographic guide. For a partially edentulous jaw without good teeth support or for a fully edentulous jaw, the CT scan may be performed with a gum-supported surgical guide (denture with markers).

Figure 20:
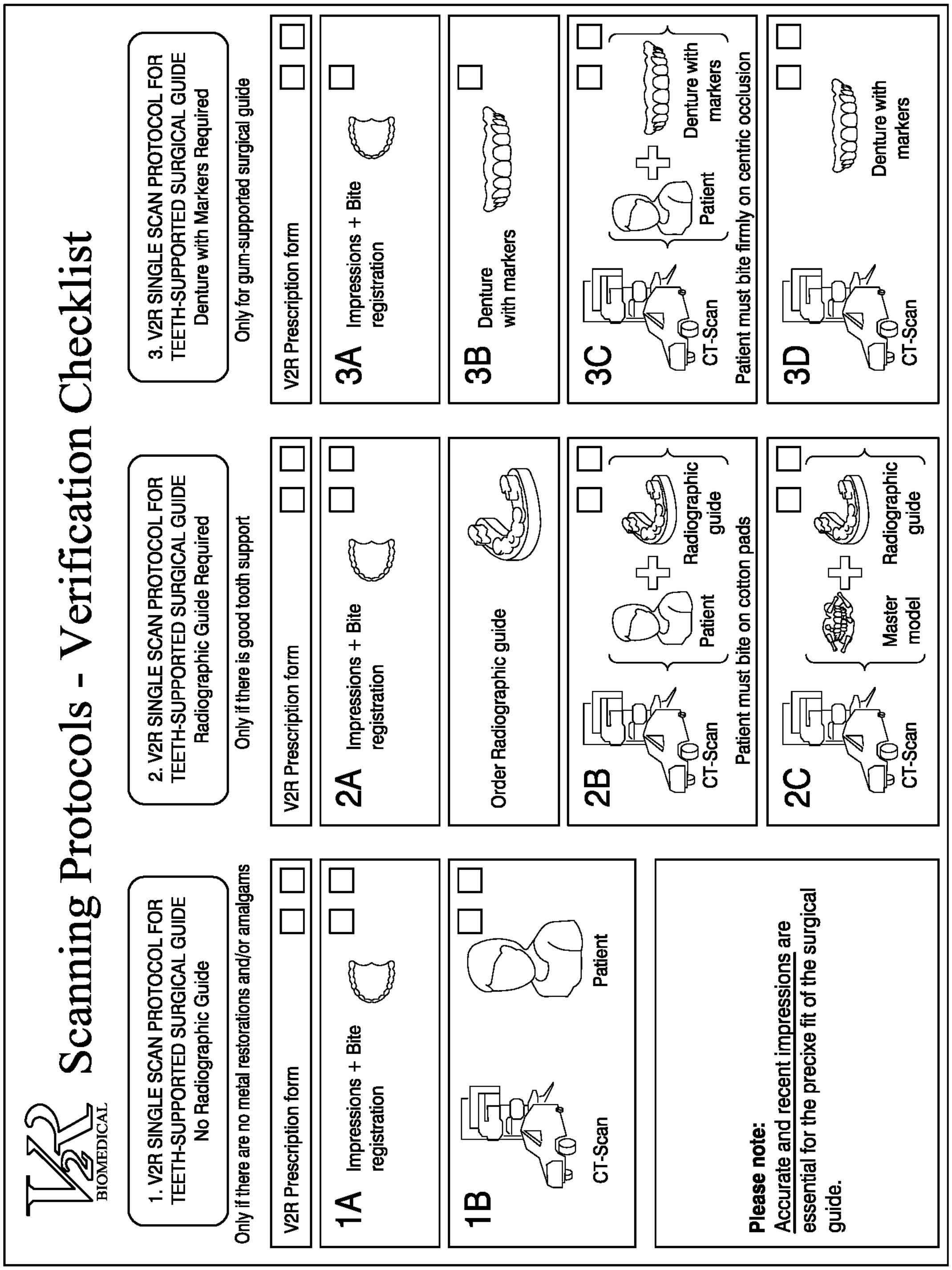
FIG. 20 shows an example of a scanning protocol verification checklist according to an embodiment of the invention.

FIG. 20 is a screenshot showing an example of a scanning protocol verification checklist according to an embodiment of the invention, illustrating different scanning protocols that can be used to create the surgical guides. The checklist includes the following separate protocols: Single-Scan Protocol for Teeth-Supported Surgical Guide, Dual Scan Protocol for Teeth-Supported Surgical Guide, and Dual Scan Protocol for Gum-Supported Surgical Guide. The Single Scan Protocol can be used if there are no metal restorations or amalgams. The Dual Scan Protocol for Teeth-Supported Surgical Guide can be used only if there is good tooth support, and the Dual Scan Protocol for Gum-Supported Surgical Guide can be used for the gum-supported surgical guide. Further, the Single Scan protocol can be used without any radiographic guide, the Dual Scan Protocol for Teeth-Supported Surgical Guide is used with a radiographic guide, and the Dual Scan Protocol for Gum-Supported Surgical Guide is used with a denture with markers.

Figure 21:
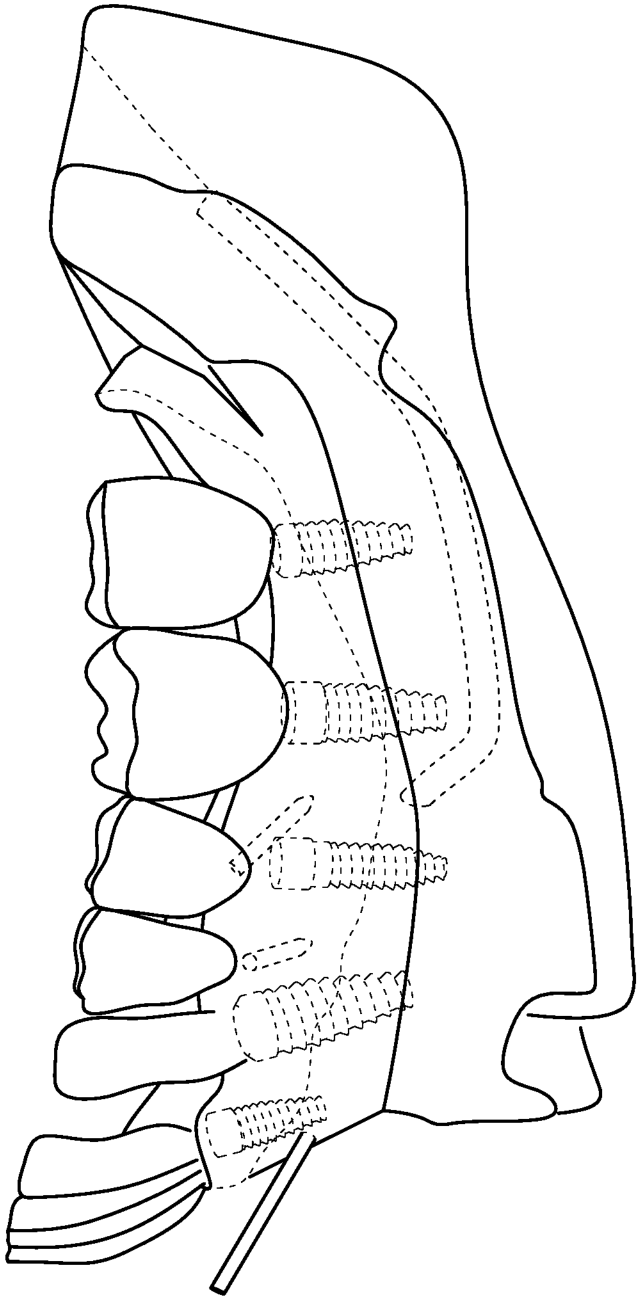
FIG. 21 is a drawing showing the placement of implants according to an embodiment of the invention.

FIG. 21 is a CAD drawing showing the placement of implants according to an embodiment of the invention.

Figure 22:
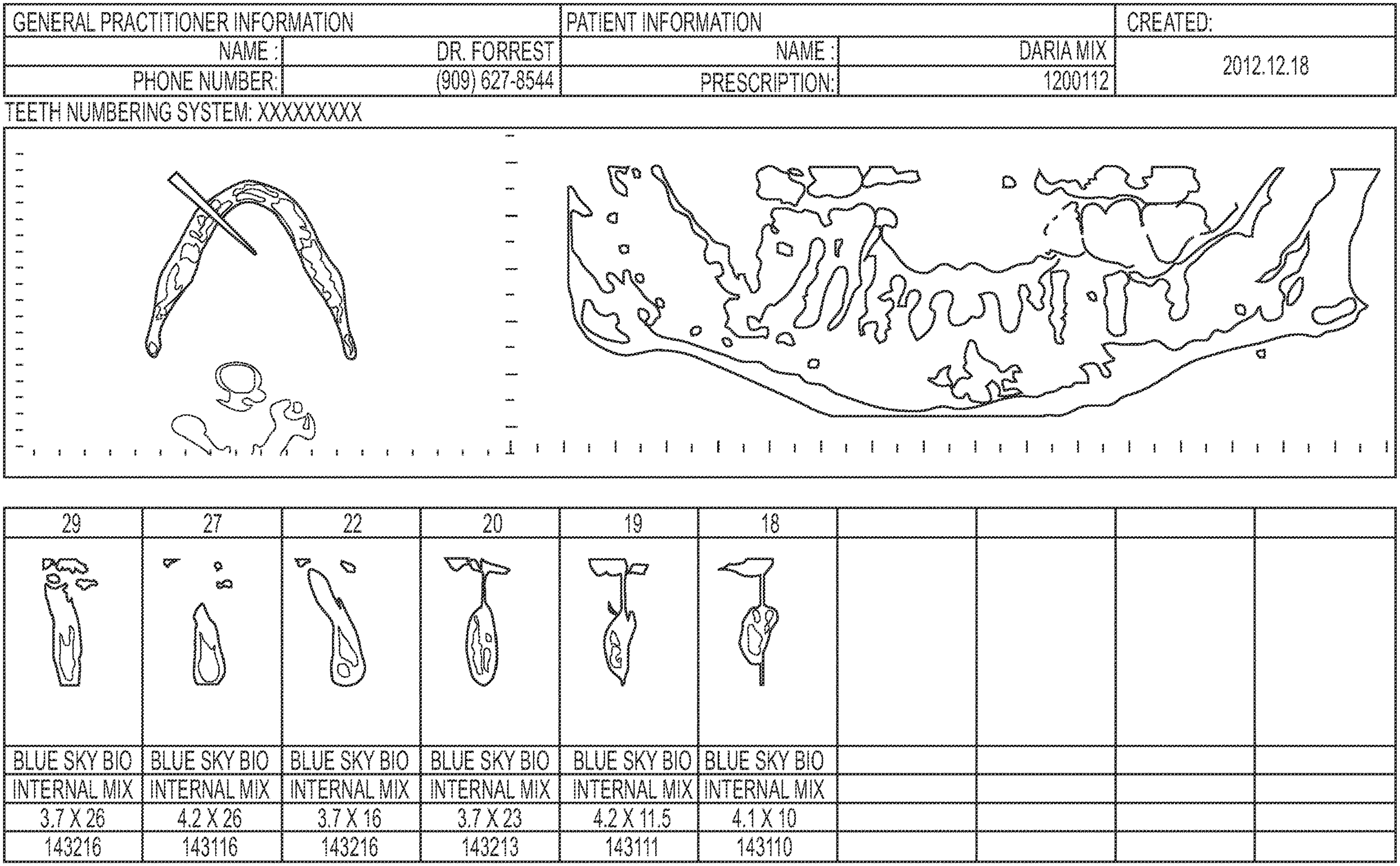
FIG. 22 shows a Treatment Planning Report Overview supplied for case analysis according to an embodiment of the invention.
Figure 23:
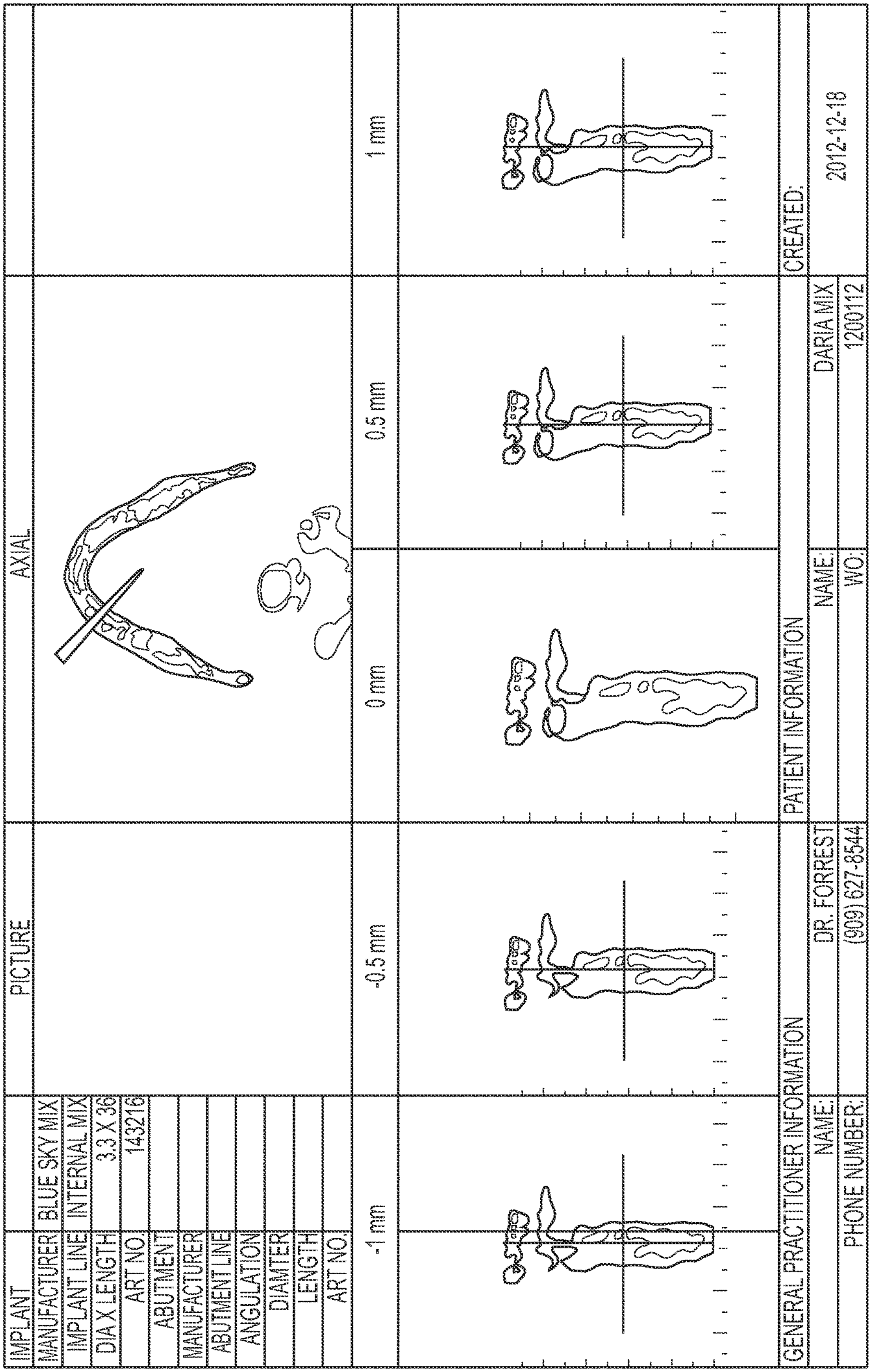
FIG. 23 shows a Planning Report for an implant site for critical evaluation according to an embodiment of the invention.

FIG. 22 is a screenshot of a Treatment Planning Report Overview supplied for case analysis according to an embodiment of the invention. The Treatment Planning Report Overview includes results of the CT scan of the whole jaw (top) as well as slices of the individual anchor or implant sites (bottom). The CT scan slices zones for each of the implant sites. If this step if not performed, the implants may be placed at divergent angles, and too much pressure may be placed on the implants and they may ultimately fail. The guide must be oriented so that the implants are not coming down through the teeth or the gums. They should be parallel and in best position in concert with the bone such that everything lines up. Based on the results of the Treatment Planning Report Overview, a Planning Report for each implant site is provided, an example of which is shown in FIG. 23.

FIG. 24 is a screenshot showing guided surgery information for a patient according to an embodiment of the invention. The surgical guide information may be developed from the CT scans shown previously. The surgical guide information includes a Complete Guided Surgery Protocol including drill selection and handles for preplanned osteotomy position. The surgical guide information includes general practitioner information, case information, and implant information including sites, implant dimensions, surgical kit, drill working length, and special notes.

FIG. 25 is a screenshot showing a treatment planning approval form according to an embodiment of the invention. The approval form includes information such as doctor information, case information, and approval method.

Figure 26B:
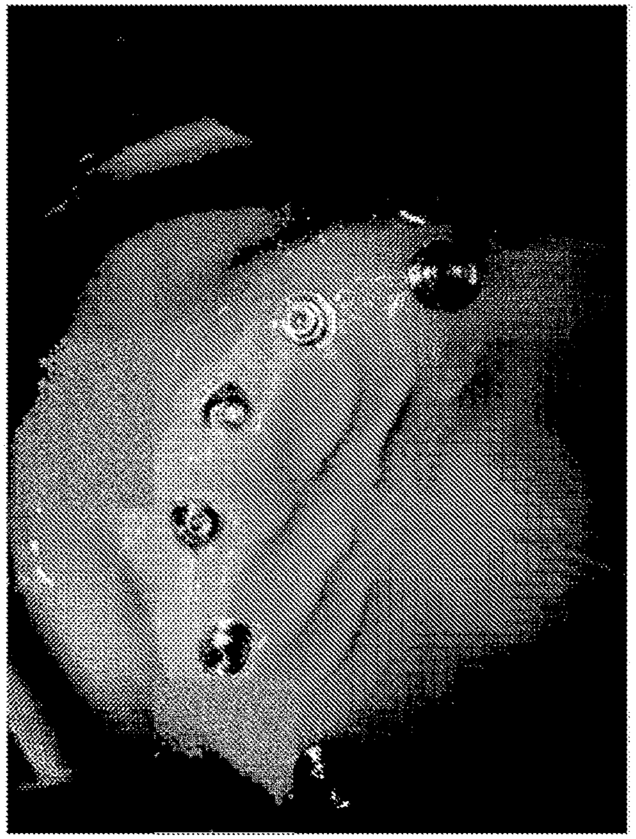
FIG. 26B is a photograph showing fast healing using a guided surgery method embodiment of the invention.
Figure 26A:
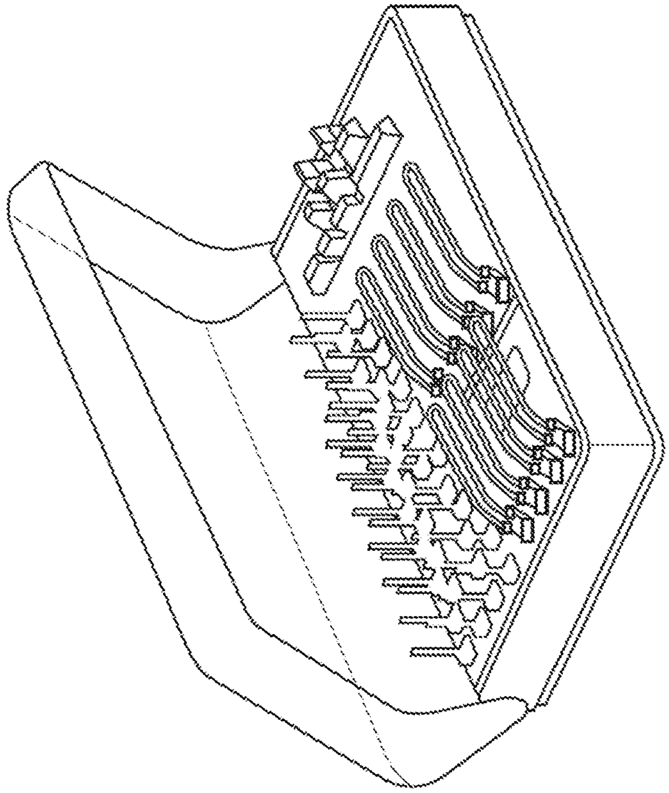
FIG. 26A shows a guided surgery kit according to an embodiment of the invention.

FIG. 26A shows a guided surgery kit according to an embodiment of the invention. It is an example of the type of guided surgery tools that can be used to drill osteotomies through the drill sites of the surgical guide.

FIG. 26B is a photograph showing fast healing using the guided surgery method embodiments of the invention. The photographs show the implants placed according to the methods of the invention.

Figure 27:
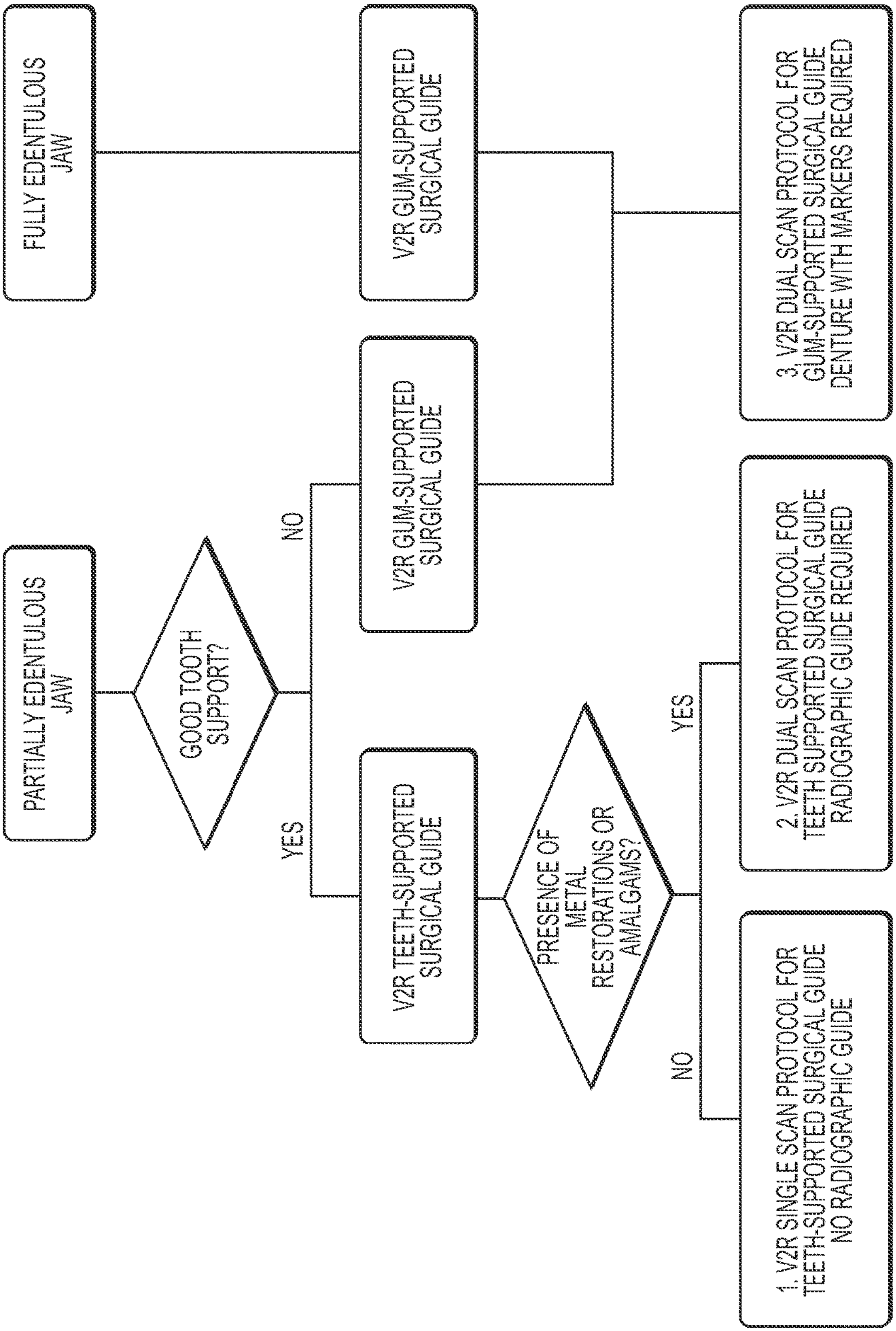
FIG. 27 is a flow chart of a decision tree to support the appropriate scanning protocol according to an embodiment of the invention.

FIG. 27 is a decision tree to support the appropriate scanning protocol according to an embodiment of the invention. The decision tree determines which scanning protocol of FIG. 20 to use. For a partially edentulous jaw, if there is good teeth support, and no metal restorations or amalgams, then the CT scan may be performed without a radiographic guide, and a single scan protocol may be used. If there is good teeth support and amalgams or metal restorations are present, then the CT scan may be performed with a radiographic guide and a dual scan protocol may be used. For a partially edentulous jaw without good teeth support or for a fully edentulous jaw, the CT scan may be performed with a gum-supported surgical guide (denture with markers), and a dual scan protocol for a sum-supported surgical guide may be used.

Figure 28A:
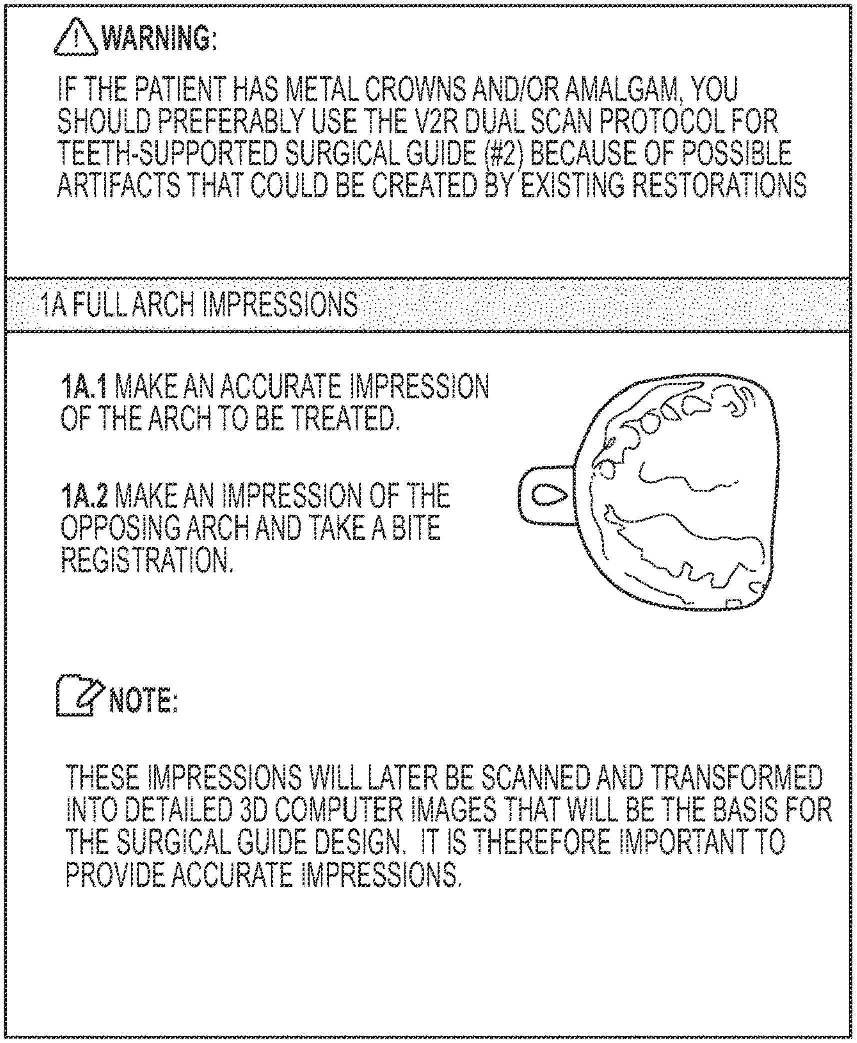
Figure 28B:
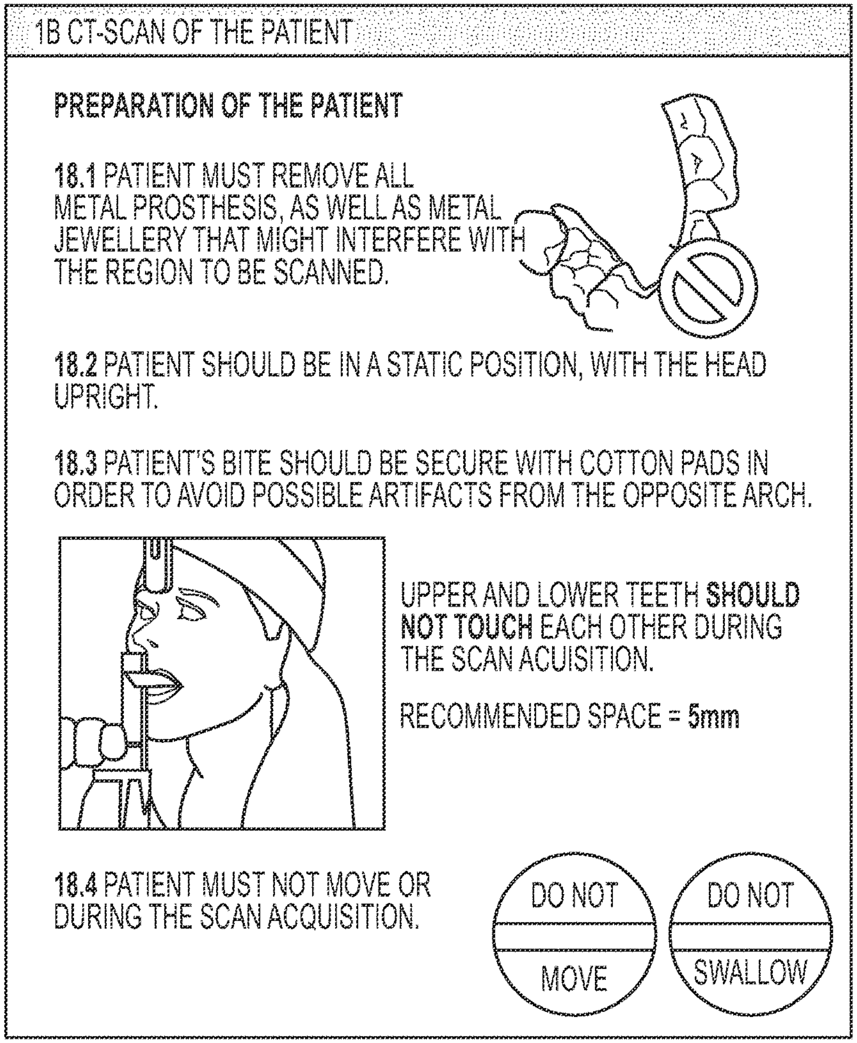

FIGS. 28A-28D are screenshots showing a Single Scan Protocol for Teeth-supported Surgical Guide according to an embodiment of the invention. First, full arch impressions of the arch to be treated and the opposite arch are taken as well as a bite registration. The arch impressions are scanned and transformed into 3D computer images and used as the basis for design of the surgical guide, as shown in FIG. 28A. Then, the patient is prepared according to the instructions in FIG. 28B, and a scan of the patient is performed. A CT scan is then performed according to the scanning instructions and parameters shown in FIG. 28C. The scanning data (DICOM files), impressions, and bite registrations are then sent to a facility and used to create a surgical guide as shown in FIG. 28D.

Figure 29A:
Figure 29B:
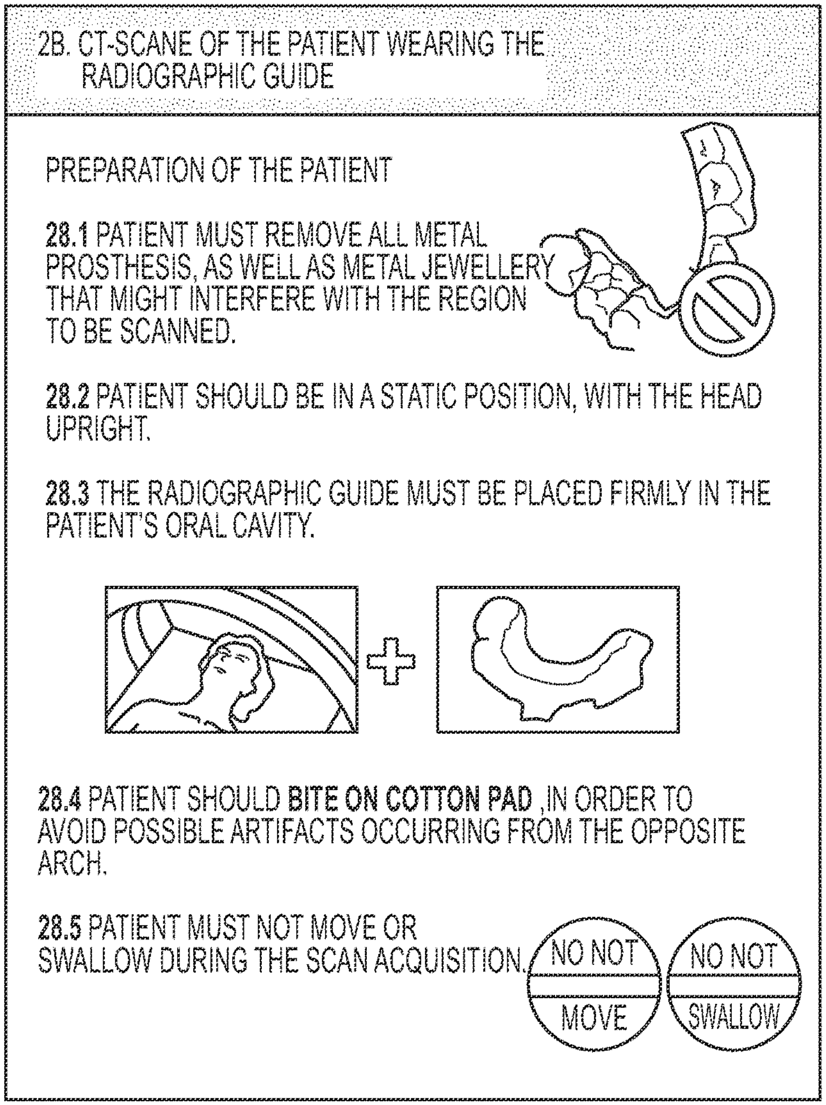
Figure 31B:
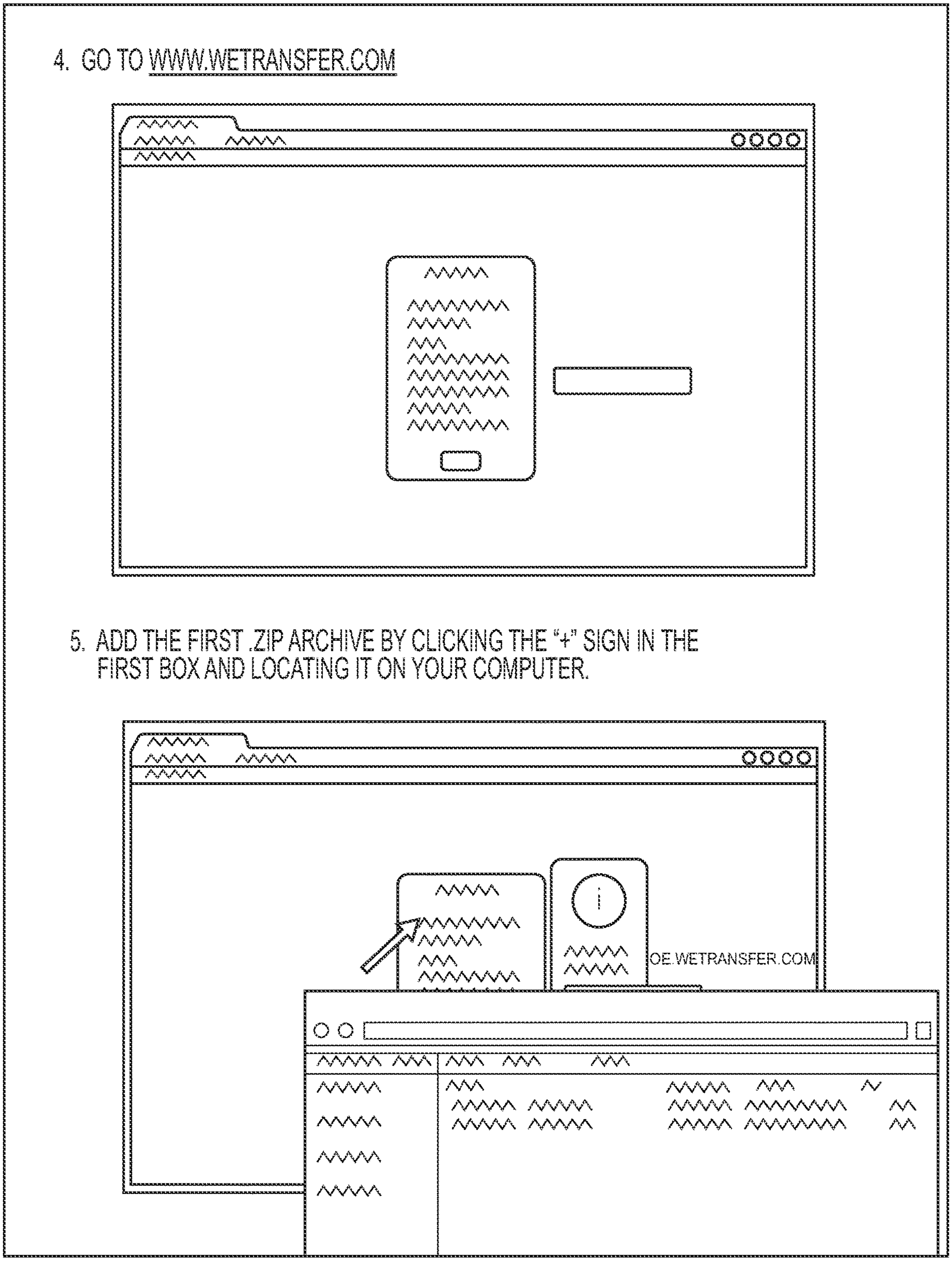

FIGS. 29A-29E are screenshots showing a Dual Scan Protocol for Teeth-supported Surgical Guide according to an embodiment of the invention. The arch impressions are scanned and transformed into 3D computer images and used as the basis for design of the surgical guide, as shown in FIG. 29A. Then, the patient is prepared according to the instructions in FIG. 29B, and a scan of the patient is performed with the radiographic guide in place according to the instructions shown in FIG. 29C. Then, a CT scan of the radiographic guide with the master model obtained from the arch impressions is performed according to the instructions in FIG. 29D. Finally, the scanning data (DICOM files), impressions, and bite registrations are then sent to a facility and used to create a surgical guide as shown in FIG. 29E.

FIGS. 30A-30F are screenshots showing a Dual Scan Protocol for Gum-Supported Surgical Guide according to an embodiment of the invention. Full arch impressions are obtained as shown in FIG. 30A, while a denture with radiopaque markers on the outer surface of the denture is created as shown in FIG. 30B. Then, the patient is prepared for a CT scan wearing the denture according to the instructions in FIG. 30C, and a scan of the patient is performed with the denture in place according to the instructions shown in FIG. 30D. A CT scan of the denture alone is performed according to the instructions in FIG. 30E. Finally, the scanning data (DICOM files) and impressions are then sent to a facility and used to create a surgical guide as shown in FIG. 30F.

FIGS. 31A-31D are screenshots showing file transfer instructions according to an embodiment of the invention. Such instructions may be used to transfer the DICOM files to a facility where a surgical guide can be created.

Figure 32:
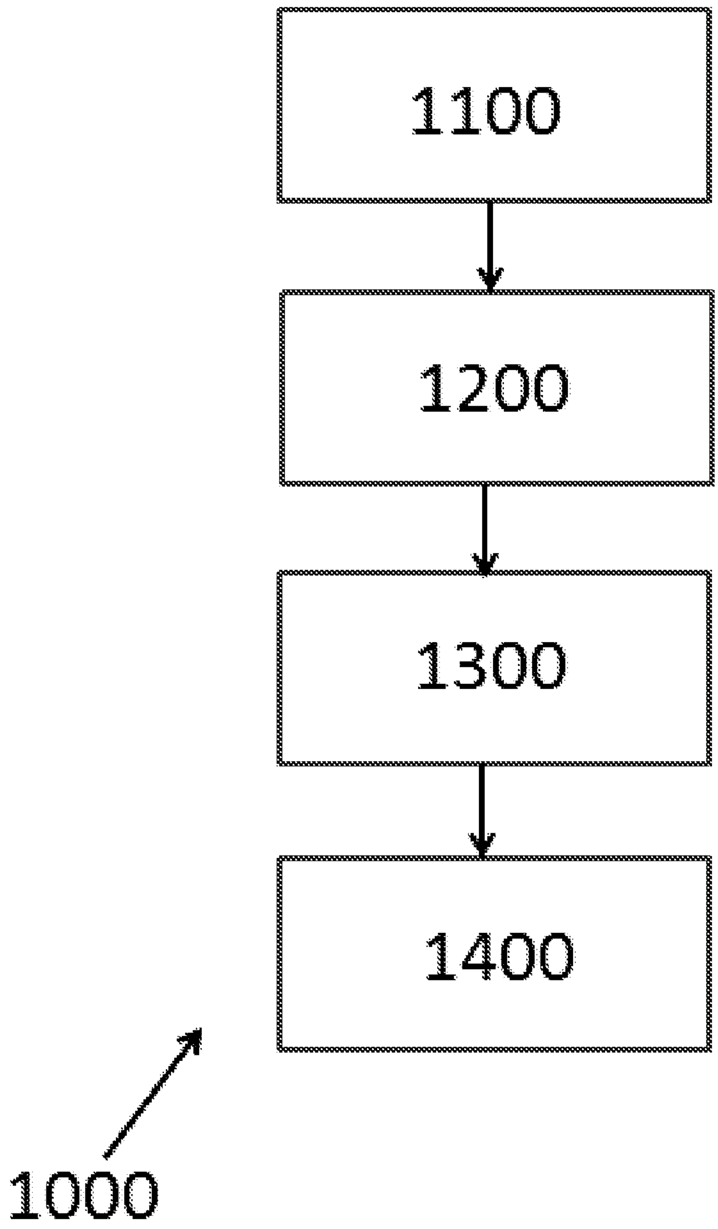
FIG. 32 is a flowchart illustrating a method for creating a surgical dental template according to an embodiment of the invention.
Figure 33:
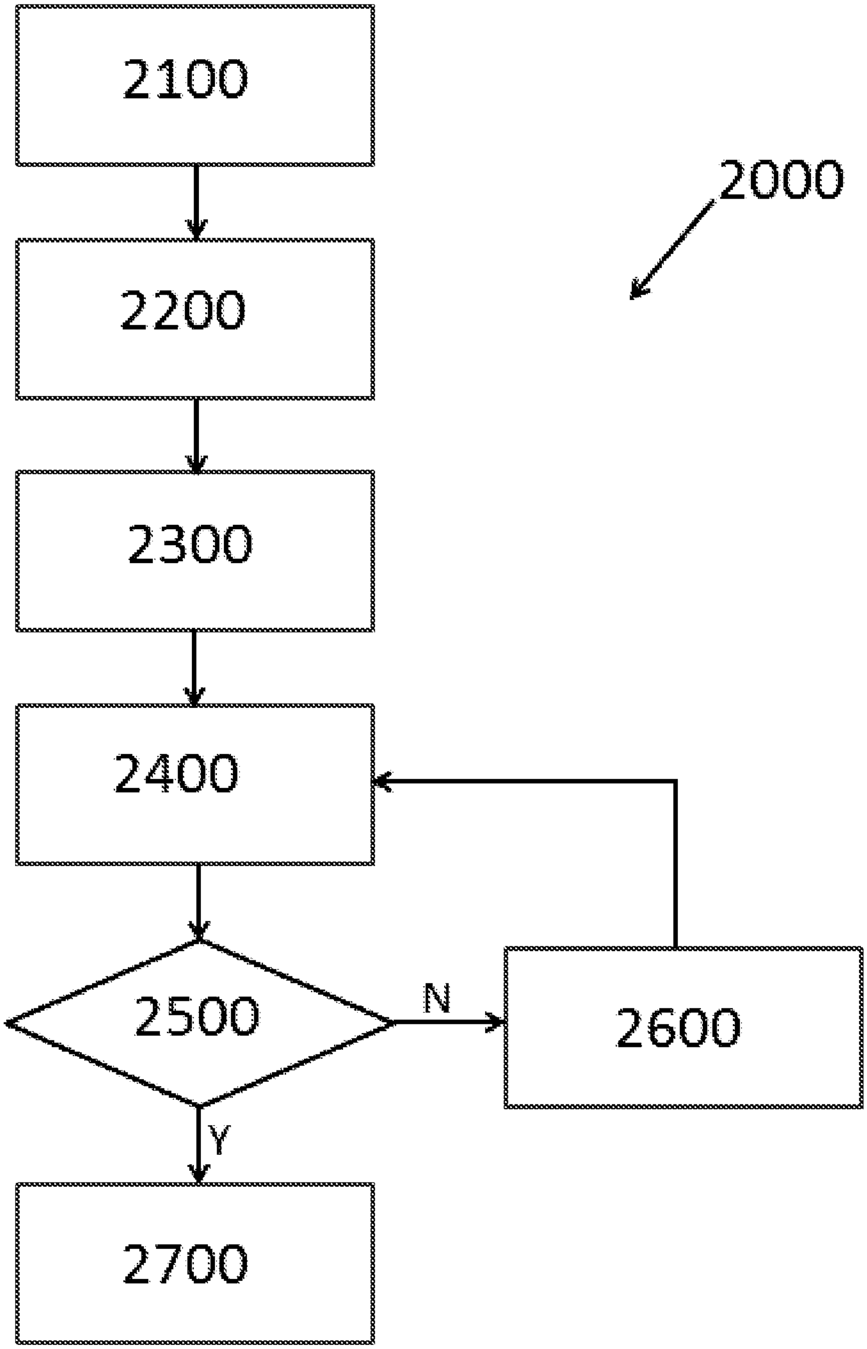
FIG. 33 is a flowchart illustrating a method for implanting a denture prosthesis in a partially edentulous patient according to an embodiment of the invention.
Figure 34:
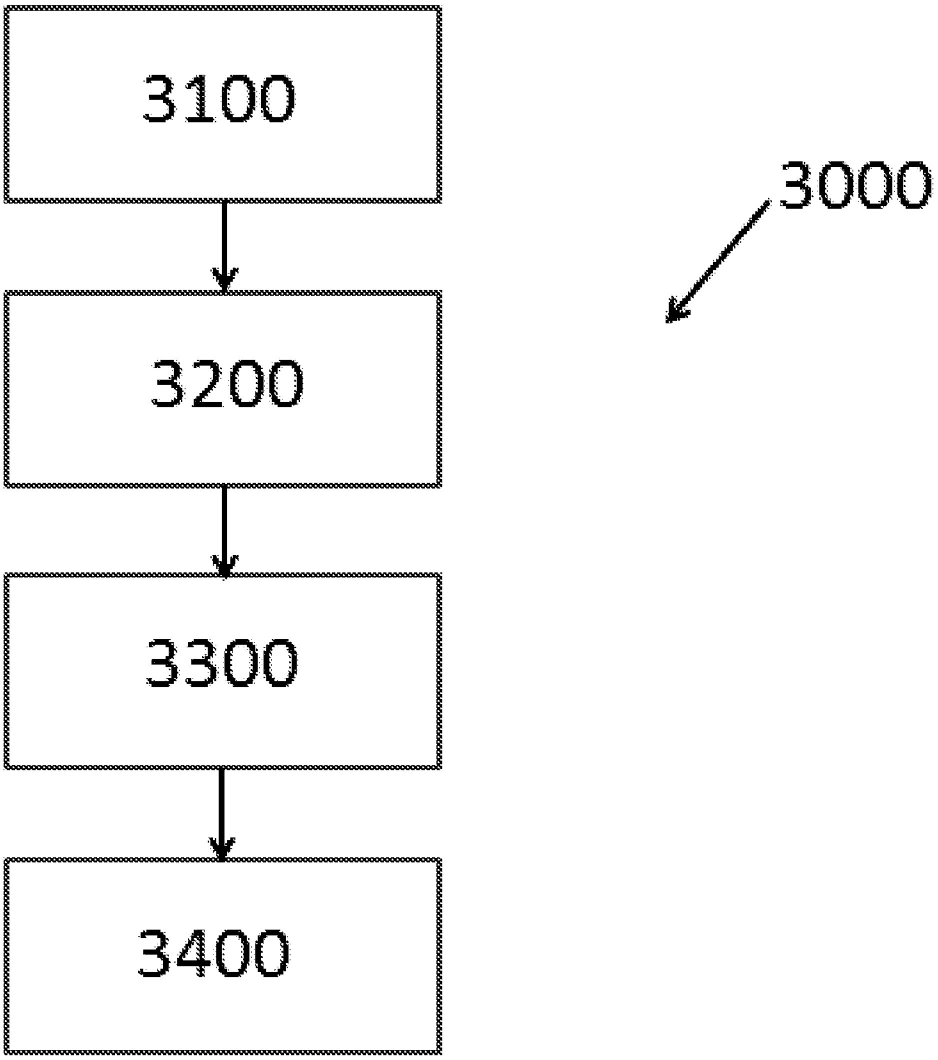
FIG. 34 is a flowchart illustrating a method for reducing jaw bone in a patient according to an embodiment of the invention.

FIGS. 32-34 refer to flowcharts illustrating exemplary methods of the invention. However, it is to be understood that the following steps may be substituted or eliminated, or performed in a different order, or additional steps may be added that fall within the scope of the invention. FIG. 32 shows an embodiment of a method 1000 for creating a surgical dental template. The method comprises performing a CT scan on a patient 1100, transferring one or more CT scan images into treatment planning software 1200, virtually placing implants in one or more positions on the CT scan using the treatment planning software 1300, and creating a surgical template based on positions on CT scan that provide one or more sites for drilling osteotomies in the maxillary or mandibular jaw for installing the implants 1400.

FIG. 33 shows an embodiment of a method 2000 for implanting a denture prosthesis in a partially edentulous patient. The method 2000 comprises providing 2100 a surgical template and a false teeth set of the invention, positioning 2200 the surgical template over the gum tissue of an edentulous jaw of a patient at a first position, inserting 2300 the false teeth set into the surgical template; instructing 2400 the patient to bite down on the false teeth set with natural teeth of the jaw opposite the edentulous jaw, confirming occlusion 2500 with the patient, and if there is no occlusion, repositioning 2600 the surgical template, and repeating until the patient confirms occlusion between the natural teeth and false teeth set; and when occlusion is confirmed, fixing 2700 the surgical template over the gum tissue of the patient's edentulous jaw at a second position.

FIG. 34 shows an embodiment of a method 3000 for reducing jaw bone in a patient. The method 3000 comprises installing 3100 a surgical template of the invention, wherein the surgical template has one or more sets of drill holes, perforating osteotomies 3200 through the drill holes in the surgical template to define markings in the jaw bone forming a boundary for reducing bone, removing the surgical template 3300 and exposing the jaw bone though an incision to reveal the osteotomies, and using a surgical instrument to remove jaw bone 2400 based on the boundary formed by the markings.

The present invention has been described with reference to particular embodiments having various features. In light of the disclosure provided above, it will be apparent to those skilled in the art that various modifications and variations can be made in the practice of the present invention without departing from the scope or spirit of the invention. One skilled in the art will recognize that the disclosed features may be used singularly, in any combination, or omitted based on the requirements and specifications of a given application or design. When an embodiment refers to "comprising" certain features, it is to be understood that the embodiments can alternatively "consist of" or "consist essentially of" any one or more of the features. Other embodiments of the invention will be apparent to those skilled in the art from consideration of the specification and practice of the invention.

It is noted in particular that where a range of values is provided in this specification, each value between the upper and lower limits of that range is also specifically disclosed. The upper and lower limits of these smaller ranges may independently be included or excluded in the range as well. The singular forms "a," "an," and "the" include plural referents unless the context clearly dictates otherwise. It is intended that the specification and examples be considered as exemplary in nature and that variations that do not depart from the essence of the invention fall within the scope of the invention. Further, all of the references cited in this disclosure are each individually incorporated by reference herein in their entireties and as such are intended to provide an efficient way of supplementing the enabling disclosure of this invention as well as provide background detailing the level of ordinary skill in the art.

The invention claimed is:

1. A dental device comprising:

a false teeth set; and a surgical template consisting of a singular structure, having a first surface including one or more drill holes for drilling osteotomies in a maxillary or mandibular jaw of a patient, the surgical template further having one or more pin holes that have an axis transverse to an axis of the one or more drill holes, wherein each of the one or more drill holes comprises a cylindrical wall that rises above said first surface and has a height which is capable of limiting drilling depth of an osteotomy in the maxillary or mandibular jaw of the patient, wherein said first surface allows for mateable attachment of the false teeth set, wherein the surgical template has a non-metallic second surface that resembles a color and appearance of gum tissue, and wherein the surgical template and false teeth set are configured to fit together to form a denture prosthesis.

2. The dental device of claim 1, wherein the surgical template is configured to fit over an edentulous patient's maxillary or mandibular gum tissue.

3. The dental device of claim 1, wherein the surgical template and false teeth set have male and female portions capable of interlocking.

4. The dental device of claim 3, wherein the surgical template comprises a male portion configured to interlock with a female portion on one tooth of the false teeth set.

5. The dental device of claim 1, wherein the surgical template comprises a ledge configured to fit the false teeth set.

6. The dental device of claim 1, wherein the surgical template further comprises one or more sets of bore holes on a front or anterior surface of said surgical template and separate from said one or more drill holes for drilling osteotomies and configured to provide a guide for reducing jaw bone when the surgical template is positioned on the maxillary or mandibular jaw during use, wherein the drill holes for drilling osteotomies are in a first direction that is configured to be substantially perpendicular to the jaw bone when in use and the bore holes are used to bore in a second direction that is configured to be substantially parallel to the jaw bone when in use and substantially perpendicular to the osteotomy drill holes.

7. The dental device of claim 1, wherein a wall of the surgical template is configured to provide the one or more pin holes.

8. The dental device of claim 7, wherein the one or more pin holes are configured as projections extending outward from the wall of the surgical template.

9. The dental device of claim 8, further comprising pins configured to pass through each of the pin holes.

10. The dental device of claim 9, wherein each pin has a handle portion extending outward from each projection and a tapered portion extending inward through each projection.

11. The dental device of claim 1, wherein the surgical template comprises one or more flanges extending outward from the template.

12. A dental device comprising:

a surgical template consisting of a singular structure, and configured to fit an interior of a maxillary or mandibular jaw over an edentulous patient's maxillary or mandibular gum tissue;

a false teeth set;

wherein the surgical template comprises a first surface including one or more drill holes for drilling osteotomies in the maxillary or mandibular jaw of the patient, wherein each of the one or more drill holes comprises a cylindrical wall that rises above said first surface and has a height which is capable of limiting drilling depth of an osteotomy in the maxillary or mandibular jaw of the patient, wherein said first surface allows for mateable attachment of the false teeth set, wherein the surgical template has a non-metallic second surface that resembles a color and appearance of gum tissue, wherein the surgical template and false teeth set are configured to fit together to form a denture prosthesis, wherein the false teeth set comprises one or more openings configured to overlap the one or more drill holes of the surgical template when the template and false teeth set are fit together, and wherein a wall of the surgical template is configured to provide one or more pin holes that have an axis transverse to an axis of the one or more drill holes.

13. The dental device of claim 12, further comprising pins configured to pass through each of the one or more pin holes.

* * * * *